(12) United States Patent
Reijerkerk et al.

(10) Patent No.: US 9,297,007 B2
(45) Date of Patent: Mar. 29, 2016

(54) MIRNAS INVOLVED IN THE BLOOD BRAIN BARRIER FUNCTION

(75) Inventors: Arie Reijerkerk, Amsterdam (NL); Helga Eveline De Vries, Amsterdam (NL)

(73) Assignee: VERENIGING VOOR CHRISTELIJK HOGER ONDERWIJS, WETENSCHAPPELIJK ONDERZOEK EN PATIENTENZORG, Amsterdam (NL)

( * ) Notice: Subject to any disclaimer, the term of this patent is extended or adjusted under 35 U.S.C. 154(b) by 274 days.

(21) Appl. No.: 13/700,624

(22) PCT Filed: May 27, 2011

(86) PCT No.: PCT/NL2011/050376
§ 371 (c)(1),
(2), (4) Date: Mar. 4, 2013

(87) PCT Pub. No.: WO2011/149354
PCT Pub. Date: Dec. 1, 2011

(65) Prior Publication Data
US 2013/0158096 A1 Jun. 20, 2013

Related U.S. Application Data

(60) Provisional application No. 61/349,337, filed on May 28, 2010.

(51) Int. Cl.
*C12N 15/113* (2010.01)
*C12Q 1/68* (2006.01)

(52) U.S. Cl.
CPC ............ *C12N 15/113* (2013.01); *C12Q 1/6876* (2013.01); *C12Q 1/6883* (2013.01); *C12N 2310/113* (2013.01); *C12N 2310/141* (2013.01); *C12Q 2600/136* (2013.01)

(58) Field of Classification Search
USPC .......................................... 514/44; 536/24.5
See application file for complete search history.

(56) References Cited

FOREIGN PATENT DOCUMENTS

| WO | 2009036332 A1 | 3/2009 |
| WO | 2009080437 A1 | 7/2009 |
| WO | 2010042831 A2 | 4/2010 |

OTHER PUBLICATIONS

Deli, Maria A. et al., "Permeability Studies on In Vitro Blood-Brain Barrier Models: Physiology, Pathology, and Pharmacology", Cellular and Molecular Neurobiology, vol. 25, No. 1, pp. 59-127, Feb. 2005.

(Continued)

*Primary Examiner* — Terra C Gibbs
(74) *Attorney, Agent, or Firm* — Browdy and Neimark, PLLC

(57) ABSTRACT

The current invention relates to use of particular nucleic acids for modulating (increasing or decreasing) blood-brain barrier function, and for use of such nucleic acids in treatment of conditions involving blood brain barrier function, including multiple sclerosis, HIV infection, Alzheimer's disease, Parkinson's disease, epilepsy, and so on. Also provided is an assay for identifying drugs useful in modulating blood brain barrier function.

16 Claims, 6 Drawing Sheets

(56) References Cited

OTHER PUBLICATIONS

Ke-Jie, Yin et al., "Peroxisome Proliferator-Activated Receptor delta Regulation of miR-5a in Ischemia-induced Cerebral Vascular Endothelial Injury", Neurobiology of Disease, Journal of Neuroscience, vol. 30, No. 18, pp. 6398-6408, May 2010.

Weksler, B. B. et al., "Blood-brain barrier-specific properties of a human adult brain endothelial cell line", The FASEB Journal, vol. 19, No. 13, pp. 1872-1874, Nov. 2005.

Seed sequence miR-30 family: ACAAAUGU

SEQUENCE LISTING

<160> NUMBER OF SEQ ID NOS: 155

<210> SEQ ID NO 1
<211> LENGTH: 23
<212> TYPE: RNA
<213> ORGANISM: Homo sapiens
<220> FEATURE:
<221> NAME/KEY: misc_feature
<223> OTHER INFORMATION: miR-886-5p

<400> SEQUENCE: 1
cgggucggag uuagcucaag cgg                                          23

<210> SEQ ID NO 2
<211> LENGTH: 22
<212> TYPE: RNA
<213> ORGANISM: Homo sapiens
<220> FEATURE:
<221> NAME/KEY: misc_feature
<223> OTHER INFORMATION: miR-888*

<400> SEQUENCE: 2
gacugacacc ucuuugggug aa                                           22

<210> SEQ ID NO 3
<211> LENGTH: 23
<212> TYPE: RNA
<213> ORGANISM: Homo sapiens
<220> FEATURE:
<221> NAME/KEY: misc_feature
<223> OTHER INFORMATION: miR-668

<400> SEQUENCE: 3
ugucacucgg cucggcccac uac                                          23

<210> SEQ ID NO 4
<211> LENGTH: 22
<212> TYPE: RNA
<213> ORGANISM: Homo sapiens
<220> FEATURE:

```
<221> NAME/KEY: misc_feature
<223> OTHER INFORMATION: miR-519d

<400> SEQUENCE: 4
caaagugccu cccuuuagag ug                                                22

<210> SEQ ID NO 5
<211> LENGTH: 22
<212> TYPE: RNA
<213> ORGANISM: Homo sapiens
<220> FEATURE:
<221> NAME/KEY: misc_feature
<223> OTHER INFORMATION: miR-487b

<400> SEQUENCE: 5
aaucguacag ggucauccac uu                                                22

<210> SEQ ID NO 6
<211> LENGTH: 22
<212> TYPE: RNA
<213> ORGANISM: Homo sapiens
<220> FEATURE:
<221> NAME/KEY: misc_feature
<223> OTHER INFORMATION: miR-494

<400> SEQUENCE: 6
ugaaacauac acgggaaacc uc                                                22

<210> SEQ ID NO 7
<211> LENGTH: 21
<212> TYPE: RNA
<213> ORGANISM: Homo sapiens
<220> FEATURE:
<221> NAME/KEY: misc_feature
<223> OTHER INFORMATION: miR-106b

<400> SEQUENCE: 7
uaaagugcug acagugcaga u                                                 21

<210> SEQ ID NO 8
<211> LENGTH: 21
<212> TYPE: RNA
<213> ORGANISM: Homo sapiens
<220> FEATURE:
<221> NAME/KEY: misc_feature
<223> OTHER INFORMATION: miR-1259

<400> SEQUENCE: 8
auauaugaug acuuagcuuu u                                                 21

<210> SEQ ID NO 9
<211> LENGTH: 22
<212> TYPE: RNA
<213> ORGANISM: Homo sapiens
<220> FEATURE:
<221> NAME/KEY: misc_feature
<223> OTHER INFORMATION: miR-100

<400> SEQUENCE: 9
aacccguaga uccgaacuug ug                                                22

<210> SEQ ID NO 10
<211> LENGTH: 21
<212> TYPE: RNA
<213> ORGANISM: Homo sapiens
<220> FEATURE:
<221> NAME/KEY: misc_feature
```

<223> OTHER INFORMATION: miR-27a

<400> SEQUENCE: 10
uucacagugg cuaaguuccg c                                          21

<210> SEQ ID NO 11
<211> LENGTH: 21
<212> TYPE: RNA
<213> ORGANISM: Homo sapiens
<220> FEATURE:
<221> NAME/KEY: misc_feature
<223> OTHER INFORMATION: miR-31

<400> SEQUENCE: 11
aggcaagaug cuggcauagc u                                          21

<210> SEQ ID NO 12
<211> LENGTH: 21
<212> TYPE: RNA
<213> ORGANISM: Homo sapiens
<220> FEATURE:
<221> NAME/KEY: misc_feature
<223> OTHER INFORMATION: MiR-889

<400> SEQUENCE: 12
uuaauaucgg acaaccauug u                                          21

<210> SEQ ID NO 13
<211> LENGTH: 22
<212> TYPE: RNA
<213> ORGANISM: Homo sapiens
<220> FEATURE:
<221> NAME/KEY: misc_feature
<223> OTHER INFORMATION: miR-26a

<400> SEQUENCE: 13
uucaaguaau ccaggauagg cu                                         22

<210> SEQ ID NO 14
<211> LENGTH: 22
<212> TYPE: RNA
<213> ORGANISM: Homo sapiens
<220> FEATURE:
<221> NAME/KEY: misc_feature
<223> OTHER INFORMATION: miR-15a

<400> SEQUENCE: 14
uagcagcaca uaaugguuug ug                                         22

<210> SEQ ID NO 15
<211> LENGTH: 21
<212> TYPE: RNA
<213> ORGANISM: Homo sapiens
<220> FEATURE:
<221> NAME/KEY: misc_feature
<223> OTHER INFORMATION: miR-126*

<400> SEQUENCE: 15
cauuauuacu uuugguacgc g                                          21

<210> SEQ ID NO 16
<211> LENGTH: 21
<212> TYPE: RNA
<213> ORGANISM: Homo sapiens
<220> FEATURE:
<221> NAME/KEY: misc_feature
<223> OTHER INFORMATION: miR-195

```
<400> SEQUENCE: 16
uagcagcaca gaaauauugg c                                              21

<210> SEQ ID NO 17
<211> LENGTH: 22
<212> TYPE: RNA
<213> ORGANISM: Homo sapiens
<220> FEATURE:
<221> NAME/KEY: misc_feature
<223> OTHER INFORMATION: MiR-24-1*

<400> SEQUENCE: 17
ugccuacuga gcugauauca gu                                             22

<210> SEQ ID NO 18
<211> LENGTH: 22
<212> TYPE: RNA
<213> ORGANISM: Homo sapiens
<220> FEATURE:
<221> NAME/KEY: misc_feature
<223> OTHER INFORMATION: miR-15b

<400> SEQUENCE: 18
uagcagcaca ucaugguuua ca                                             22

<210> SEQ ID NO 19
<211> LENGTH: 22
<212> TYPE: RNA
<213> ORGANISM: Homo sapiens
<220> FEATURE:
<221> NAME/KEY: misc_feature
<223> OTHER INFORMATION: miR-193a-3p

<400> SEQUENCE: 19
aacuggccua caaaguccca gu                                             22

<210> SEQ ID NO 20
<211> LENGTH: 21
<212> TYPE: RNA
<213> ORGANISM: Homo sapiens
<220> FEATURE:
<221> NAME/KEY: misc_feature
<223> OTHER INFORMATION: miR-551b

<400> SEQUENCE: 20
gcgacccaua cuugguuuca g                                              21

<210> SEQ ID NO 21
<211> LENGTH: 20
<212> TYPE: RNA
<213> ORGANISM: Homo sapiens
<220> FEATURE:
<221> NAME/KEY: misc_feature
<223> OTHER INFORMATION: miR-202

<400> SEQUENCE: 21
agagguauag ggcaugggaa                                                20

<210> SEQ ID NO 22
<211> LENGTH: 17
<212> TYPE: RNA
<213> ORGANISM: Homo sapiens
<220> FEATURE:
<221> NAME/KEY: misc_feature
<223> OTHER INFORMATION: miR-1274b
```

```
<400> SEQUENCE: 22
ucccuguucg ggcgcca                                                  17

<210> SEQ ID NO 23
<211> LENGTH: 17
<212> TYPE: RNA
<213> ORGANISM: Homo sapiens
<220> FEATURE:
<221> NAME/KEY: misc_feature
<223> OTHER INFORMATION: miR-1275

<400> SEQUENCE: 23
gugggggaga ggcuguc                                                  17

<210> SEQ ID NO 24
<211> LENGTH: 23
<212> TYPE: RNA
<213> ORGANISM: Homo sapiens
<220> FEATURE:
<221> NAME/KEY: misc_feature
<223> OTHER INFORMATION: miR-19a

<400> SEQUENCE: 24
ugugcaaauc uaugcaaaac uga                                           23

<210> SEQ ID NO 25
<211> LENGTH: 22
<212> TYPE: RNA
<213> ORGANISM: Homo sapiens
<220> FEATURE:
<221> NAME/KEY: misc_feature
<223> OTHER INFORMATION: let-7g

<400> SEQUENCE: 25
ugagguagua guuuguacag uu                                            22

<210> SEQ ID NO 26
<211> LENGTH: 23
<212> TYPE: RNA
<213> ORGANISM: Homo sapiens
<220> FEATURE:
<221> NAME/KEY: misc_feature
<223> OTHER INFORMATION: miR-18b

<400> SEQUENCE: 26
uaaggugcau cuagugcagu uag                                           23

<210> SEQ ID NO 27
<211> LENGTH: 22
<212> TYPE: RNA
<213> ORGANISM: Homo sapiens
<220> FEATURE:
<221> NAME/KEY: misc_feature
<223> OTHER INFORMATION: miR-29c

<400> SEQUENCE: 27
uagcaccauu ugaaaucggu ua                                            22

<210> SEQ ID NO 28
<211> LENGTH: 22
<212> TYPE: RNA
<213> ORGANISM: Homo sapiens
<220> FEATURE:
<221> NAME/KEY: misc_feature
<223> OTHER INFORMATION: miR-874

<400> SEQUENCE: 28
```

```
cugcccuggc ccgagggacc ga                                              22

<210> SEQ ID NO 29
<211> LENGTH: 18
<212> TYPE: RNA
<213> ORGANISM: Homo sapiens
<220> FEATURE:
<221> NAME/KEY: misc_feature
<223> OTHER INFORMATION: miR-1274a

<400> SEQUENCE: 29
gucccuguuc aggcgcca                                                   18

<210> SEQ ID NO 30
<211> LENGTH: 21
<212> TYPE: RNA
<213> ORGANISM: Homo sapiens
<220> FEATURE:
<221> NAME/KEY: misc_feature
<223> OTHER INFORMATION: miR-1908

<400> SEQUENCE: 30
cggcggggac ggcgauuggu c                                               21

<210> SEQ ID NO 31
<211> LENGTH: 22
<212> TYPE: RNA
<213> ORGANISM: Homo sapiens
<220> FEATURE:
<221> NAME/KEY: misc_feature
<223> OTHER INFORMATION: miR-887

<400> SEQUENCE: 31
gugaacgggc gccaucccga gg                                              22

<210> SEQ ID NO 32
<211> LENGTH: 22
<212> TYPE: RNA
<213> ORGANISM: Homo sapiens
<220> FEATURE:
<221> NAME/KEY: misc_feature
<223> OTHER INFORMATION: miR-30b

<400> SEQUENCE: 32
uguaaacauc cuacacucag cu                                              22

<210> SEQ ID NO 33
<211> LENGTH: 23
<212> TYPE: RNA
<213> ORGANISM: Homo sapiens
<220> FEATURE:
<221> NAME/KEY: misc_feature
<223> OTHER INFORMATION: miR-106a

<400> SEQUENCE: 33
aaaagugcuu acagugcagg uag                                             23

<210> SEQ ID NO 34
<211> LENGTH: 22
<212> TYPE: RNA
<213> ORGANISM: Homo sapiens
<220> FEATURE:
<221> NAME/KEY: misc_feature
<223> OTHER INFORMATION: miR-584

<400> SEQUENCE: 34
```

```
uuaugguuug ccugggacug ag                                      22

<210> SEQ ID NO 35
<211> LENGTH: 22
<212> TYPE: RNA
<213> ORGANISM: Homo sapiens
<220> FEATURE:
<221> NAME/KEY: misc_feature
<223> OTHER INFORMATION: let-7b

<400> SEQUENCE: 35
ugagguagua gguugugugg uu                                      22

<210> SEQ ID NO 36
<211> LENGTH: 18
<212> TYPE: RNA
<213> ORGANISM: Homo sapiens
<220> FEATURE:
<221> NAME/KEY: misc_feature
<223> OTHER INFORMATION: miR-1260

<400> SEQUENCE: 36
aucccaccuc ugccacca                                           18

<210> SEQ ID NO 37
<211> LENGTH: 23
<212> TYPE: RNA
<213> ORGANISM: Homo sapiens
<220> FEATURE:
<221> NAME/KEY: misc_feature
<223> OTHER INFORMATION: miR-30c

<400> SEQUENCE: 37
uguaaacauc cuacacucuc agc                                     23

<210> SEQ ID NO 38
<211> LENGTH: 22
<212> TYPE: RNA
<213> ORGANISM: Homo sapiens
<220> FEATURE:
<221> NAME/KEY: misc_feature
<223> OTHER INFORMATION: miR-30e

<400> SEQUENCE: 38
uguaaacauc cuugacugga ag                                      22

<210> SEQ ID NO 39
<211> LENGTH: 22
<212> TYPE: RNA
<213> ORGANISM: Homo sapiens
<220> FEATURE:
<221> NAME/KEY: misc_feature
<223> OTHER INFORMATION: let-7e

<400> SEQUENCE: 39
ugagguagga gguuguauag uu                                      22

<210> SEQ ID NO 40
<211> LENGTH: 23
<212> TYPE: RNA
<213> ORGANISM: Homo sapiens
<220> FEATURE:
<221> NAME/KEY: misc_feature
<223> OTHER INFORMATION: miR-19b

<400> SEQUENCE: 40
ugugcaaauc caugcaaaac uga                                     23
```

```
<210> SEQ ID NO 41
<211> LENGTH: 23
<212> TYPE: RNA
<213> ORGANISM: Homo sapiens
<220> FEATURE:
<221> NAME/KEY: misc_feature
<223> OTHER INFORMATION: miR-221

<400> SEQUENCE: 41
agcuacauug ucugcugggu uuc                                              23

<210> SEQ ID NO 42
<211> LENGTH: 21
<212> TYPE: RNA
<213> ORGANISM: Homo sapiens
<220> FEATURE:
<221> NAME/KEY: misc_feature
<223> OTHER INFORMATION: miR-221
<220> FEATURE:
<221> NAME/KEY: misc_feature
<223> OTHER INFORMATION: miR-25*

<400> SEQUENCE: 42
aggcggagac uugggcaauu g                                                21

<210> SEQ ID NO 43
<211> LENGTH: 21
<212> TYPE: RNA
<213> ORGANISM: Homo sapiens
<220> FEATURE:
<221> NAME/KEY: misc_feature
<223> OTHER INFORMATION: miR-26b

<400> SEQUENCE: 43
uucaaguaau ucaggauagg u                                                21

<210> SEQ ID NO 44
<211> LENGTH: 23
<212> TYPE: RNA
<213> ORGANISM: Homo sapiens
<220> FEATURE:
<221> NAME/KEY: misc_feature
<223> OTHER INFORMATION: miR-423-5p

<400> SEQUENCE: 44
ugaggggcag agagcgagac uuu                                              23

<210> SEQ ID NO 45
<211> LENGTH: 23
<212> TYPE: RNA
<213> ORGANISM: Homo sapiens
<220> FEATURE:
<221> NAME/KEY: misc_feature
<223> OTHER INFORMATION: miR-18a

<400> SEQUENCE: 45
uaaggugcau cuagugcaga uag                                              23

<210> SEQ ID NO 46
<211> LENGTH: 22
<212> TYPE: RNA
<213> ORGANISM: Homo sapiens
<220> FEATURE:
<221> NAME/KEY: misc_feature
<223> OTHER INFORMATION: let-7d

<400> SEQUENCE: 46
```

-continued agagguagua gguugcauag uu                                              22

<210> SEQ ID NO 47
<211> LENGTH: 22
<212> TYPE: RNA
<213> ORGANISM: Homo sapiens
<220> FEATURE:
<221> NAME/KEY: misc_feature
<223> OTHER INFORMATION: let-7c

<400> SEQUENCE: 47
ugagguagua gguuguaugg uu                                              22

<210> SEQ ID NO 48
<211> LENGTH: 23
<212> TYPE: RNA
<213> ORGANISM: Homo sapiens
<220> FEATURE:
<221> NAME/KEY: misc_feature
<223> OTHER INFORMATION: miR-17

<400> SEQUENCE: 48
caaagugcuu acagugcagg uag                                             23

<210> SEQ ID NO 49
<211> LENGTH: 22
<212> TYPE: RNA
<213> ORGANISM: Homo sapiens
<220> FEATURE:
<221> NAME/KEY: misc_feature
<223> OTHER INFORMATION: miR-1284

<400> SEQUENCE: 49
ucuauacaga cccuggcuuu uc                                              22

<210> SEQ ID NO 50
<211> LENGTH: 22
<212> TYPE: RNA
<213> ORGANISM: Homo sapiens
<220> FEATURE:
<221> NAME/KEY: misc_feature
<223> OTHER INFORMATION: miR-424

<400> SEQUENCE: 50
cagcagcaau ucauguuuug aa                                              22

<210> SEQ ID NO 51
<211> LENGTH: 22
<212> TYPE: RNA
<213> ORGANISM: Homo sapiens
<220> FEATURE:
<221> NAME/KEY: misc_feature
<223> OTHER INFORMATION: miR-374a

<400> SEQUENCE: 51
uuauaauaca accugauaag ug                                              22

<210> SEQ ID NO 52
<211> LENGTH: 23
<212> TYPE: RNA
<213> ORGANISM: Homo sapiens
<220> FEATURE:
<221> NAME/KEY: misc_feature
<223> OTHER INFORMATION: miR-29b

<400> SEQUENCE: 52
uagcaccauu ugaaaucagu guu         23

<210> SEQ ID NO 53
<211> LENGTH: 22
<212> TYPE: RNA
<213> ORGANISM: Homo sapiens
<220> FEATURE:
<221> NAME/KEY: misc_feature
<223> OTHER INFORMATION: miR-30d

<400> SEQUENCE: 53
uguaaacauc cccgacugga ag         22

<210> SEQ ID NO 54
<211> LENGTH: 22
<212> TYPE: RNA
<213> ORGANISM: Homo sapiens
<220> FEATURE:
<221> NAME/KEY: misc_feature
<223> OTHER INFORMATION: miR-634

<400> SEQUENCE: 54
aaccagcacc ccaacuuugg ac         22

<210> SEQ ID NO 55
<211> LENGTH: 22
<212> TYPE: RNA
<213> ORGANISM: Homo sapiens
<220> FEATURE:
<221> NAME/KEY: misc_feature
<223> OTHER INFORMATION: miR-1285

<400> SEQUENCE: 55
ucugggcaac aaagugagac cu         22

<210> SEQ ID NO 56
<211> LENGTH: 18
<212> TYPE: RNA
<213> ORGANISM: Homo sapiens
<220> FEATURE:
<221> NAME/KEY: misc_feature
<223> OTHER INFORMATION: miR-1308

<400> SEQUENCE: 56
gcaugggugg uucagugg         18

<210> SEQ ID NO 57
<211> LENGTH: 22
<212> TYPE: RNA
<213> ORGANISM: Homo sapiens
<220> FEATURE:
<221> NAME/KEY: misc_feature
<223> OTHER INFORMATION: miR-138-1*

<400> SEQUENCE: 57
gcuacuucac aacaccaggg cc         22

<210> SEQ ID NO 58
<211> LENGTH: 22
<212> TYPE: RNA
<213> ORGANISM: Homo sapiens
<220> FEATURE:
<221> NAME/KEY: misc_feature
<223> OTHER INFORMATION: miR-381

<400> SEQUENCE: 58
uauacaaggg caagcucucu gu         22

```
<210> SEQ ID NO 59
<211> LENGTH: 21
<212> TYPE: RNA
<213> ORGANISM: Homo sapiens
<220> FEATURE:
<221> NAME/KEY: misc_feature
<223> OTHER INFORMATION: miR-222

<400> SEQUENCE: 59
agcuacaucu ggcuacuggg u                                              21

<210> SEQ ID NO 60
<211> LENGTH: 21
<212> TYPE: RNA
<213> ORGANISM: Homo sapiens
<220> FEATURE:
<221> NAME/KEY: misc_feature
<223> OTHER INFORMATION: miR-27b

<400> SEQUENCE: 60
uucacagugg cuaaguucug c                                              21

<210> SEQ ID NO 61
<211> LENGTH: 23
<212> TYPE: RNA
<213> ORGANISM: Homo sapiens
<220> FEATURE:
<221> NAME/KEY: misc_feature
<223> OTHER INFORMATION: miR-20b

<400> SEQUENCE: 61
caaagugcuc auagugcagg uag                                            23

<210> SEQ ID NO 62
<211> LENGTH: 22
<212> TYPE: RNA
<213> ORGANISM: Homo sapiens
<220> FEATURE:
<221> NAME/KEY: misc_feature
<223> OTHER INFORMATION: miR-130a

<400> SEQUENCE: 62
cagugcaaug uuaaaagggc au                                             22

<210> SEQ ID NO 63
<211> LENGTH: 22
<212> TYPE: RNA
<213> ORGANISM: Homo sapiens
<220> FEATURE:
<221> NAME/KEY: misc_feature
<223> OTHER INFORMATION: miR-129*

<400> SEQUENCE: 63
aagcccuuac cccaaaaagu au                                             22

<210> SEQ ID NO 64
<211> LENGTH: 23
<212> TYPE: RNA
<213> ORGANISM: Homo sapiens
<220> FEATURE:
<221> NAME/KEY: misc_feature
<223> OTHER INFORMATION: miR-103

<400> SEQUENCE: 64
agcagcauug uacagggcua uga                                            23
```

```
<210> SEQ ID NO 65
<211> LENGTH: 23
<212> TYPE: RNA
<213> ORGANISM: Homo sapiens
<220> FEATURE:
<221> NAME/KEY: misc_feature
<223> OTHER INFORMATION: miR-301a

<400> SEQUENCE: 65
cagugcaaua guauugucaa agc                                              23

<210> SEQ ID NO 66
<211> LENGTH: 22
<212> TYPE: RNA
<213> ORGANISM: Homo sapiens
<220> FEATURE:
<221> NAME/KEY: misc_feature
<223> OTHER INFORMATION: miR-766

<400> SEQUENCE: 66
acuccagccc cacagccuca gc                                               22

<210> SEQ ID NO 67
<211> LENGTH: 21
<212> TYPE: RNA
<213> ORGANISM: Homo sapiens
<220> FEATURE:
<221> NAME/KEY: misc_feature
<223> OTHER INFORMATION: miR-101

<400> SEQUENCE: 67
uacaguacug ugauaacuga a                                                21

<210> SEQ ID NO 68
<211> LENGTH: 22
<212> TYPE: RNA
<213> ORGANISM: Homo sapiens
<220> FEATURE:
<221> NAME/KEY: misc_feature
<223> OTHER INFORMATION: miR-933

<400> SEQUENCE: 68
ugugcgcagg gagaccucuc cc                                               22

<210> SEQ ID NO 69
<211> LENGTH: 23
<212> TYPE: RNA
<213> ORGANISM: Homo sapiens
<220> FEATURE:
<221> NAME/KEY: misc_feature
<223> OTHER INFORMATION: miR-107

<400> SEQUENCE: 69
agcagcauug uacagggcua uca                                              23

<210> SEQ ID NO 70
<211> LENGTH: 21
<212> TYPE: RNA
<213> ORGANISM: Homo sapiens
<220> FEATURE:
<221> NAME/KEY: misc_feature
<223> OTHER INFORMATION: miR-33a

<400> SEQUENCE: 70
gugcauugua guugcauugc a                                                21
```

```
<210> SEQ ID NO 71
<211> LENGTH: 23
<212> TYPE: RNA
<213> ORGANISM: Homo sapiens
<220> FEATURE:
<221> NAME/KEY: misc_feature
<223> OTHER INFORMATION: miR-105

<400> SEQUENCE: 71
ucaaaugcuc agacuccugu ggu                                           23

<210> SEQ ID NO 72
<211> LENGTH: 23
<212> TYPE: RNA
<213> ORGANISM: Homo sapiens
<220> FEATURE:
<221> NAME/KEY: misc_feature
<223> OTHER INFORMATION: miR-20a

<400> SEQUENCE: 72
uaaagugcuu auagugcagg uag                                           23

<210> SEQ ID NO 73
<211> LENGTH: 21
<212> TYPE: RNA
<213> ORGANISM: Homo sapiens
<220> FEATURE:
<221> NAME/KEY: misc_feature
<223> OTHER INFORMATION: miR-151-5p

<400> SEQUENCE: 73
ucgaggagcu cacagucuag u                                             21

<210> SEQ ID NO 74
<211> LENGTH: 22
<212> TYPE: RNA
<213> ORGANISM: Homo sapiens
<220> FEATURE:
<221> NAME/KEY: misc_feature
<223> OTHER INFORMATION: miR-320a

<400> SEQUENCE: 74
aaaagcuggg uugagagggc ga                                            22

<210> SEQ ID NO 75
<211> LENGTH: 22
<212> TYPE: RNA
<213> ORGANISM: Homo sapiens
<220> FEATURE:
<221> NAME/KEY: misc_feature
<223> OTHER INFORMATION: miR-31*

<400> SEQUENCE: 75
ugcuaugcca acauauugcc au                                            22

<210> SEQ ID NO 76
<211> LENGTH: 20
<212> TYPE: RNA
<213> ORGANISM: Homo sapiens
<220> FEATURE:
<221> NAME/KEY: misc_feature
<223> OTHER INFORMATION: miR-665

<400> SEQUENCE: 76
accaggaggc ugaggcccu                                                20

<210> SEQ ID NO 77
```

```
<211> LENGTH: 22
<212> TYPE: RNA
<213> ORGANISM: Homo sapiens
<220> FEATURE:
<221> NAME/KEY: misc_feature
<223> OTHER INFORMATION: let-7a

<400> SEQUENCE: 77
ugagguagua gguuguauag uu                                              22

<210> SEQ ID NO 78
<211> LENGTH: 21
<212> TYPE: RNA
<213> ORGANISM: Homo sapiens
<220> FEATURE:
<221> NAME/KEY: misc_feature
<223> OTHER INFORMATION: miR-149*

<400> SEQUENCE: 78
agggagggac gggggcugug c                                               21

<210> SEQ ID NO 79
<211> LENGTH: 22
<212> TYPE: RNA
<213> ORGANISM: Homo sapiens
<220> FEATURE:
<221> NAME/KEY: misc_feature
<223> OTHER INFORMATION: miR-519e*

<400> SEQUENCE: 79
uucuccaaaa gggagcacuu uc                                              22

<210> SEQ ID NO 80
<211> LENGTH: 22
<212> TYPE: RNA
<213> ORGANISM: Homo sapiens
<220> FEATURE:
<221> NAME/KEY: misc_feature
<223> OTHER INFORMATION: miR-30a

<400> SEQUENCE: 80
uguaaacauc cucgacugga ag                                              22

<210> SEQ ID NO 81
<211> LENGTH: 23
<212> TYPE: RNA
<213> ORGANISM: Homo sapiens
<220> FEATURE:
<221> NAME/KEY: misc_feature
<223> OTHER INFORMATION: miR-93

<400> SEQUENCE: 81
caaagugcug uucgugcagg uag                                             23

<210> SEQ ID NO 82
<211> LENGTH: 22
<212> TYPE: RNA
<213> ORGANISM: Homo sapiens
<220> FEATURE:
<221> NAME/KEY: misc_feature
<223> OTHER INFORMATION: miR-32

<400> SEQUENCE: 82
uauugcacau uacuaaguug ca                                              22

<210> SEQ ID NO 83
<211> LENGTH: 18
```

```
<212> TYPE: RNA
<213> ORGANISM: Homo sapiens
<220> FEATURE:
<221> NAME/KEY: misc_feature
<223> OTHER INFORMATION: miR-1827

<400> SEQUENCE: 83
ugaggcagua gauugaau                                                       18

<210> SEQ ID NO 84
<211> LENGTH: 22
<212> TYPE: RNA
<213> ORGANISM: Homo sapiens
<220> FEATURE:
<221> NAME/KEY: misc_feature
<223> OTHER INFORMATION: miR-184

<400> SEQUENCE: 84
uggacggaga acugauaagg gu                                                  22

<210> SEQ ID NO 85
<211> LENGTH: 21
<212> TYPE: RNA
<213> ORGANISM: Homo sapiens
<220> FEATURE:
<221> NAME/KEY: misc_feature
<223> OTHER INFORMATION: miR-23a

<400> SEQUENCE: 85
aucacauugc cagggauuuc c                                                   21

<210> SEQ ID NO 86
<211> LENGTH: 23
<212> TYPE: RNA
<213> ORGANISM: Homo sapiens
<220> FEATURE:
<221> NAME/KEY: misc_feature
<223> OTHER INFORMATION: miR-1184

<400> SEQUENCE: 86
ccugcagcga cuugauggcu ucc                                                 23

<210> SEQ ID NO 87
<211> LENGTH: 23
<212> TYPE: RNA
<213> ORGANISM: Homo sapiens
<220> FEATURE:
<221> NAME/KEY: misc_feature
<223> OTHER INFORMATION: miR-454

<400> SEQUENCE: 87
uagugcaaua uugcuuauag ggu                                                 23

<210> SEQ ID NO 88
<211> LENGTH: 22
<212> TYPE: RNA
<213> ORGANISM: Homo sapiens
<220> FEATURE:
<221> NAME/KEY: misc_feature
<223> OTHER INFORMATION: miR-130b

<400> SEQUENCE: 88
cagugcaaug augaaagggc au                                                  22

<210> SEQ ID NO 89
<211> LENGTH: 22
<212> TYPE: RNA
```

```
<213> ORGANISM: Homo sapiens
<220> FEATURE:
<221> NAME/KEY: misc_feature
<223> OTHER INFORMATION: miR-1265

<400> SEQUENCE: 89
caggaugugg ucaaguguug uu                                          22

<210> SEQ ID NO 90
<211> LENGTH: 24
<212> TYPE: RNA
<213> ORGANISM: Homo sapiens
<220> FEATURE:
<221> NAME/KEY: misc_feature
<223> OTHER INFORMATION: miR-1201

<400> SEQUENCE: 90
agccugauua aacacaugcu cuga                                        24

<210> SEQ ID NO 91
<211> LENGTH: 22
<212> TYPE: RNA
<213> ORGANISM: Homo sapiens
<220> FEATURE:
<221> NAME/KEY: misc_feature
<223> OTHER INFORMATION: miR-99b

<400> SEQUENCE: 91
cacccguaga accgaccuug cg                                          22

<210> SEQ ID NO 92
<211> LENGTH: 18
<212> TYPE: RNA
<213> ORGANISM: Homo sapiens
<220> FEATURE:
<221> NAME/KEY: misc_feature
<223> OTHER INFORMATION: miR-513a-5p

<400> SEQUENCE: 92
uucacaggga ggugucau                                               18

<210> SEQ ID NO 93
<211> LENGTH: 22
<212> TYPE: RNA
<213> ORGANISM: Homo sapiens
<220> FEATURE:
<221> NAME/KEY: misc_feature
<223> OTHER INFORMATION: miR-185

<400> SEQUENCE: 93
uggagagaaa ggcaguuccu ga                                          22

<210> SEQ ID NO 94
<211> LENGTH: 22
<212> TYPE: RNA
<213> ORGANISM: Homo sapiens
<220> FEATURE:
<221> NAME/KEY: misc_feature
<223> OTHER INFORMATION: miR-24

<400> SEQUENCE: 94
uggcucaguu cagcaggaac ag                                          22

<210> SEQ ID NO 95
<211> LENGTH: 23
<212> TYPE: RNA
<213> ORGANISM: Homo sapiens
```

```
<220> FEATURE:
<221> NAME/KEY: misc_feature
<223> OTHER INFORMATION: miR-191

<400> SEQUENCE: 95
caacggaauc ccaaaagcag cug                                          23

<210> SEQ ID NO 96
<211> LENGTH: 22
<212> TYPE: RNA
<213> ORGANISM: Homo sapiens
<220> FEATURE:
<221> NAME/KEY: misc_feature
<223> OTHER INFORMATION: miR-29a

<400> SEQUENCE: 96
uagcaccauc ugaaaucggu ua                                           22

<210> SEQ ID NO 97
<211> LENGTH: 22
<212> TYPE: RNA
<213> ORGANISM: Homo sapiens
<220> FEATURE:
<221> NAME/KEY: misc_feature
<223> OTHER INFORMATION: miR-22

<400> SEQUENCE: 97
aagcugccag uugaagaacu gu                                           22

<210> SEQ ID NO 98
<211> LENGTH: 22
<212> TYPE: RNA
<213> ORGANISM: Homo sapiens
<220> FEATURE:
<221> NAME/KEY: misc_feature
<223> OTHER INFORMATION: miR-34a

<400> SEQUENCE: 98
uggcaguguc uuagcugguu gu                                           22

<210> SEQ ID NO 99
<211> LENGTH: 22
<212> TYPE: RNA
<213> ORGANISM: Homo sapiens
<220> FEATURE:
<221> NAME/KEY: misc_feature
<223> OTHER INFORMATION: miR-491-3p

<400> SEQUENCE: 99
cuuaugcaag auucccuucu ac                                           22

<210> SEQ ID NO 100
<211> LENGTH: 21
<212> TYPE: RNA
<213> ORGANISM: Homo sapiens
<220> FEATURE:
<221> NAME/KEY: misc_feature
<223> OTHER INFORMATION: miR-140-3p

<400> SEQUENCE: 100
uaccacaggg uagaaccacg g                                            21

<210> SEQ ID NO 101
<211> LENGTH: 21
<212> TYPE: RNA
<213> ORGANISM: Homo sapiens
<220> FEATURE:
```

```
<221> NAME/KEY: misc_feature
<223> OTHER INFORMATION: miR-628-3p

<400> SEQUENCE: 101
ucuaguaaga guggcagucg a                                              21

<210> SEQ ID NO 102
<211> LENGTH: 22
<212> TYPE: RNA
<213> ORGANISM: Homo sapiens
<220> FEATURE:
<221> NAME/KEY: misc_feature
<223> OTHER INFORMATION: miR-340

<400> SEQUENCE: 102
uuauaaagca augagacuga uu                                             22

<210> SEQ ID NO 103
<211> LENGTH: 22
<212> TYPE: RNA
<213> ORGANISM: Homo sapiens
<220> FEATURE:
<221> NAME/KEY: misc_feature
<223> OTHER INFORMATION: miR-34b

<400> SEQUENCE: 103
caaucacuaa cuccacugcc au                                             22

<210> SEQ ID NO 104
<211> LENGTH: 22
<212> TYPE: RNA
<213> ORGANISM: Homo sapiens
<220> FEATURE:
<221> NAME/KEY: misc_feature
<223> OTHER INFORMATION: miR-25

<400> SEQUENCE: 104
cauugcacuu gucucggucu ga                                             22

<210> SEQ ID NO 105
<211> LENGTH: 23
<212> TYPE: RNA
<213> ORGANISM: Homo sapiens
<220> FEATURE:
<221> NAME/KEY: misc_feature
<223> OTHER INFORMATION: miR-181a

<400> SEQUENCE: 105
aacauucaac gcugucggug agu                                            23

<210> SEQ ID NO 106
<211> LENGTH: 22
<212> TYPE: RNA
<213> ORGANISM: Homo sapiens
<220> FEATURE:
<221> NAME/KEY: misc_feature
<223> OTHER INFORMATION: miR-320b

<400> SEQUENCE: 106
aaaagcuggg uugagagggc aa                                             22

<210> SEQ ID NO 107
<211> LENGTH: 19
<212> TYPE: RNA
<213> ORGANISM: Homo sapiens
<220> FEATURE:
<221> NAME/KEY: misc_feature
```

-continued

```
<223> OTHER INFORMATION: miR-320d

<400> SEQUENCE: 107
aaaagcuggg uugagagga                                                    19

<210> SEQ ID NO 108
<211> LENGTH: 23
<212> TYPE: RNA
<213> ORGANISM: Homo sapiens
<220> FEATURE:
<221> NAME/KEY: misc_feature
<223> OTHER INFORMATION: miR-1255a

<400> SEQUENCE: 108
aggaugagca aagaaaguag auu                                               23

<210> SEQ ID NO 109
<211> LENGTH: 22
<212> TYPE: RNA
<213> ORGANISM: Homo sapiens
<220> FEATURE:
<221> NAME/KEY: misc_feature
<223> OTHER INFORMATION: miR-183*

<400> SEQUENCE: 109
gugaauuacc gaagggccau aa                                                22

<210> SEQ ID NO 110
<211> LENGTH: 23
<212> TYPE: RNA
<213> ORGANISM: Homo sapiens
<220> FEATURE:
<221> NAME/KEY: misc_feature
<223> OTHER INFORMATION: miR-664

<400> SEQUENCE: 110
uauucauuua uccccagccu aca                                               23

<210> SEQ ID NO 111
<211> LENGTH: 22
<212> TYPE: RNA
<213> ORGANISM: Homo sapiens
<220> FEATURE:
<221> NAME/KEY: misc_feature
<223> OTHER INFORMATION: miR-32*

<400> SEQUENCE: 111
caauuuagug ugugugauau uu                                                22

<210> SEQ ID NO 112
<211> LENGTH: 22
<212> TYPE: RNA
<213> ORGANISM: Homo sapiens
<220> FEATURE:
<221> NAME/KEY: misc_feature
<223> OTHER INFORMATION: miR-574-3p

<400> SEQUENCE: 112
cacgcucaug cacacaccca ca                                                22

<210> SEQ ID NO 113
<211> LENGTH: 21
<212> TYPE: RNA
<213> ORGANISM: Homo sapiens
<220> FEATURE:
<221> NAME/KEY: misc_feature
<223> OTHER INFORMATION: miR-525-5p
```

```
<400> SEQUENCE: 113
cuccagaggg augcacuuuc u                                              21

<210> SEQ ID NO 114
<211> LENGTH: 23
<212> TYPE: RNA
<213> ORGANISM: Homo sapiens
<220> FEATURE:
<221> NAME/KEY: misc_feature
<223> OTHER INFORMATION: miR-423-3p

<400> SEQUENCE: 114
agcucggucu gaggcccuc agu                                             23

<210> SEQ ID NO 115
<211> LENGTH: 22
<212> TYPE: RNA
<213> ORGANISM: Homo sapiens
<220> FEATURE:
<221> NAME/KEY: misc_feature
<223> OTHER INFORMATION: miR-519e

<400> SEQUENCE: 115
aagugccucc uuuuagagug uu                                             22

<210> SEQ ID NO 116
<211> LENGTH: 21
<212> TYPE: RNA
<213> ORGANISM: Homo sapiens
<220> FEATURE:
<221> NAME/KEY: misc_feature
<223> OTHER INFORMATION: miR-23b

<400> SEQUENCE: 116
aucacauugc cagggauuac c                                              21

<210> SEQ ID NO 117
<211> LENGTH: 22
<212> TYPE: RNA
<213> ORGANISM: Homo sapiens
<220> FEATURE:
<221> NAME/KEY: misc_feature
<223> OTHER INFORMATION: miR-30e*

<400> SEQUENCE: 117
cuuucagucg gauguuuaca gc                                             22

<210> SEQ ID NO 118
<211> LENGTH: 21
<212> TYPE: RNA
<213> ORGANISM: Homo sapiens
<220> FEATURE:
<221> NAME/KEY: misc_feature
<223> OTHER INFORMATION: miR-549

<400> SEQUENCE: 118
ugacaacuau ggaugagcuc u                                              21

<210> SEQ ID NO 119
<211> LENGTH: 21
<212> TYPE: RNA
<213> ORGANISM: Homo sapiens
<220> FEATURE:
<221> NAME/KEY: misc_feature
<223> OTHER INFORMATION: miR-886-3p
```

-continued

<400> SEQUENCE: 119
cgcgggugcu uacugacccu u                                              21

<210> SEQ ID NO 120
<211> LENGTH: 23
<212> TYPE: RNA
<213> ORGANISM: Homo sapiens
<220> FEATURE:
<221> NAME/KEY: misc_feature
<223> OTHER INFORMATION: miR-339-5p

<400> SEQUENCE: 120
ucccuguccu ccaggagcuc acg                                            23

<210> SEQ ID NO 121
<211> LENGTH: 21
<212> TYPE: RNA
<213> ORGANISM: Homo sapiens
<220> FEATURE:
<221> NAME/KEY: misc_feature
<223> OTHER INFORMATION: miR-331-3p

<400> SEQUENCE: 121
gccccugggc cuauccuaga a                                              21

<210> SEQ ID NO 122
<211> LENGTH: 22
<212> TYPE: RNA
<213> ORGANISM: Homo sapiens
<220> FEATURE:
<221> NAME/KEY: misc_feature
<223> OTHER INFORMATION: miR-589

<400> SEQUENCE: 122
ugagaaccac gucugcucug ag                                             22

<210> SEQ ID NO 123
<211> LENGTH: 21
<212> TYPE: RNA
<213> ORGANISM: Homo sapiens
<220> FEATURE:
<221> NAME/KEY: misc_feature
<223> OTHER INFORMATION: miR-765

<400> SEQUENCE: 123
uggaggagaa ggaaggugau g                                              21

<210> SEQ ID NO 124
<211> LENGTH: 22
<212> TYPE: RNA
<213> ORGANISM: Homo sapiens
<220> FEATURE:
<221> NAME/KEY: misc_feature
<223> OTHER INFORMATION: miR-663

<400> SEQUENCE: 124
aggcggggcg ccgcgggacc gc                                             22

<210> SEQ ID NO 125
<211> LENGTH: 23
<212> TYPE: RNA
<213> ORGANISM: Homo sapiens
<220> FEATURE:
<221> NAME/KEY: misc_feature
<223> OTHER INFORMATION: miR-155

<400> SEQUENCE: 125

```
uuaaugcuaa ucgugauagg ggu                                           23

<210> SEQ ID NO 126
<211> LENGTH: 23
<212> TYPE: RNA
<213> ORGANISM: Homo sapiens
<220> FEATURE:
<221> NAME/KEY: misc_feature
<223> OTHER INFORMATION: miR-1264

<400> SEQUENCE: 126
caagucuuau uugagcaccu guu                                           23

<210> SEQ ID NO 127
<211> LENGTH: 20
<212> TYPE: RNA
<213> ORGANISM: Homo sapiens
<220> FEATURE:
<221> NAME/KEY: misc_feature
<223> OTHER INFORMATION: miR-320c

<400> SEQUENCE: 127
aaaagcuggg uugagagggu                                               20

<210> SEQ ID NO 128
<211> LENGTH: 19
<212> TYPE: RNA
<213> ORGANISM: Homo sapiens
<220> FEATURE:
<221> NAME/KEY: misc_feature
<223> OTHER INFORMATION: miR-1290

<400> SEQUENCE: 128
uggauuuuug gaucaggga                                                19

<210> SEQ ID NO 129
<211> LENGTH: 22
<212> TYPE: RNA
<213> ORGANISM: Homo sapiens
<220> FEATURE:
<221> NAME/KEY: misc_feature
<223> OTHER INFORMATION: miR-374b

<400> SEQUENCE: 129
auauaauaca accugcuaag ug                                            22

<210> SEQ ID NO 130
<211> LENGTH: 23
<212> TYPE: RNA
<213> ORGANISM: Homo sapiens
<220> FEATURE:
<221> NAME/KEY: misc_feature
<223> OTHER INFORMATION: miR-492

<400> SEQUENCE: 130
aggaccugcg ggacaagauu cuu                                           23

<210> SEQ ID NO 131
<211> LENGTH: 22
<212> TYPE: RNA
<213> ORGANISM: Homo sapiens
<220> FEATURE:
<221> NAME/KEY: misc_feature
<223> OTHER INFORMATION: miR-362-3p

<400> SEQUENCE: 131
```
aacacaccua uucaaggauu ca                                              22

<210> SEQ ID NO 132
<211> LENGTH: 22
<212> TYPE: RNA
<213> ORGANISM: Homo sapiens
<220> FEATURE:
<221> NAME/KEY: misc_feature
<223> OTHER INFORMATION: miR-197

<400> SEQUENCE: 132
uucaccaccu ucuccaccca gc                                              22

<210> SEQ ID NO 133
<211> LENGTH: 23
<212> TYPE: RNA
<213> ORGANISM: Homo sapiens
<220> FEATURE:
<221> NAME/KEY: misc_feature
<223> OTHER INFORMATION: miR-574-5p

<400> SEQUENCE: 133
ugagugugug ugugugagug ugu                                             23

<210> SEQ ID NO 134
<211> LENGTH: 22
<212> TYPE: RNA
<213> ORGANISM: Homo sapiens
<220> FEATURE:
<221> NAME/KEY: misc_feature
<223> OTHER INFORMATION: miR-148b

<400> SEQUENCE: 134
ucagugcauc acagaacuuu gu                                              22

<210> SEQ ID NO 135
<211> LENGTH: 21
<212> TYPE: RNA
<213> ORGANISM: Homo sapiens
<220> FEATURE:
<221> NAME/KEY: misc_feature
<223> OTHER INFORMATION: miR-151-3p

<400> SEQUENCE: 135
cuagacugaa gcuccuugag g                                               21

<210> SEQ ID NO 136
<211> LENGTH: 20
<212> TYPE: RNA
<213> ORGANISM: Homo sapiens
<220> FEATURE:
<221> NAME/KEY: misc_feature
<223> OTHER INFORMATION: miR-520d-5p

<400> SEQUENCE: 136
cuacaaaggg aagcccuuuc                                                 20

<210> SEQ ID NO 137
<211> LENGTH: 21
<212> TYPE: RNA
<213> ORGANISM: Homo sapiens
<220> FEATURE:
<221> NAME/KEY: misc_feature
<223> OTHER INFORMATION: miR-151-3p

<400> SEQUENCE: 137
cuagacugaa gcuccuugag g                                               21

```
<210> SEQ ID NO 138
<211> LENGTH: 23
<212> TYPE: RNA
<213> ORGANISM: Homo sapiens
<220> FEATURE:
<221> NAME/KEY: misc_feature
<223> OTHER INFORMATION: miR-675

<400> SEQUENCE: 138
uggugcggag agggcccaca gug                                            23

<210> SEQ ID NO 139
<211> LENGTH: 22
<212> TYPE: RNA
<213> ORGANISM: Homo sapiens
<220> FEATURE:
<221> NAME/KEY: misc_feature
<223> OTHER INFORMATION: miR-625*

<400> SEQUENCE: 139
gacuauagaa cuucccccu ca                                              22

<210> SEQ ID NO 140
<211> LENGTH: 23
<212> TYPE: RNA
<213> ORGANISM: Homo sapiens
<220> FEATURE:
<221> NAME/KEY: misc_feature
<223> OTHER INFORMATION: miR-516a-5p

<400> SEQUENCE: 140
uucucgagga aagaagcacu uuc                                            23

<210> SEQ ID NO 141
<211> LENGTH: 21
<212> TYPE: RNA
<213> ORGANISM: Homo sapiens
<220> FEATURE:
<221> NAME/KEY: misc_feature
<223> OTHER INFORMATION: miR-129-5p

<400> SEQUENCE: 141
cuuuuugcgg ucugggcuug c                                              21

<210> SEQ ID NO 142
<211> LENGTH: 19
<212> TYPE: RNA
<213> ORGANISM: Homo sapiens
<220> FEATURE:
<221> NAME/KEY: misc_feature
<223> OTHER INFORMATION: miR-1246

<400> SEQUENCE: 142
aauggauuuu uggagcagg                                                 19

<210> SEQ ID NO 143
<211> LENGTH: 22
<212> TYPE: RNA
<213> ORGANISM: Homo sapiens
<220> FEATURE:
<221> NAME/KEY: misc_feature
<223> OTHER INFORMATION: miR-193b

<400> SEQUENCE: 143
aacuggcccu caaagucccg cu                                             22
```

```
<210> SEQ ID NO 144
<211> LENGTH: 17
<212> TYPE: RNA
<213> ORGANISM: Homo sapiens
<220> FEATURE:
<221> NAME/KEY: misc_feature
<223> OTHER INFORMATION: miR-1297

<400> SEQUENCE: 144
uucaaguaau ucaggug                                                    17

<210> SEQ ID NO 145
<211> LENGTH: 23
<212> TYPE: RNA
<213> ORGANISM: Homo sapiens
<220> FEATURE:
<221> NAME/KEY: misc_feature
<223> OTHER INFORMATION: miR-7

<400> SEQUENCE: 145
uggaagacua gugauuuugu ugu                                             23

<210> SEQ ID NO 146
<211> LENGTH: 22
<212> TYPE: RNA
<213> ORGANISM: Homo sapiens
<220> FEATURE:
<221> NAME/KEY: misc_feature
<223> OTHER INFORMATION: miR-214

<400> SEQUENCE: 146
acagcaggca cagacaggca gu                                              22

<210> SEQ ID NO 147
<211> LENGTH: 22
<212> TYPE: RNA
<213> ORGANISM: Homo sapiens
<220> FEATURE:
<221> NAME/KEY: misc_feature
<223> OTHER INFORMATION: miR-509-3-5p

<400> SEQUENCE: 147
uacugcagac guggcaauca ug                                              22

<210> SEQ ID NO 148
<211> LENGTH: 22
<212> TYPE: RNA
<213> ORGANISM: Homo sapiens
<220> FEATURE:
<221> NAME/KEY: misc_feature
<223> OTHER INFORMATION: miR-744

<400> SEQUENCE: 148
ugcggggcua gggcuaacag ca                                              22

<210> SEQ ID NO 149
<211> LENGTH: 20
<212> TYPE: RNA
<213> ORGANISM: Homo sapiens
<220> FEATURE:
<221> NAME/KEY: misc_feature
<223> OTHER INFORMATION: miR-518a-5p/miR-527

<400> SEQUENCE: 149
```

```
cugcaaaggg aagcccuuuc                                                    20

<210> SEQ ID NO 150
<211> LENGTH: 23
<212> TYPE: RNA
<213> ORGANISM: Homo sapiens
<220> FEATURE:
<221> NAME/KEY: misc_feature
<223> OTHER INFORMATION: miR-498

<400> SEQUENCE: 150
uuucaagcca gggggcguuu uuc                                                23

<210> SEQ ID NO 151
<211> LENGTH: 22
<212> TYPE: RNA
<213> ORGANISM: Homo sapiens
<220> FEATURE:
<221> NAME/KEY: misc_feature
<223> OTHER INFORMATION: miR-183

<400> SEQUENCE: 151
uauggcacug guagaauuca cu                                                 22

<210> SEQ ID NO 152
<211> LENGTH: 22
<212> TYPE: RNA
<213> ORGANISM: Homo sapiens
<220> FEATURE:
<221> NAME/KEY: misc_feature
<223> OTHER INFORMATION: miR-597

<400> SEQUENCE: 152
ugugucacuc gaugaccacu gu                                                 22

<210> SEQ ID NO 153
<211> LENGTH: 70
<212> TYPE: RNA
<213> ORGANISM: Artificial Sequence
<220> FEATURE:
<223> OTHER INFORMATION: synthetic

<400> SEQUENCE: 153
gcgacuguaa acauccucga cuggaagcug ugaagcacag augggcuuuc agucggaugu        60
uugcagcugc                                                               70

<210> SEQ ID NO 154
<211> LENGTH: 22
<212> TYPE: DNA
<213> ORGANISM: Artificial Sequence
<220> FEATURE:
<223> OTHER INFORMATION: synthetic

<400> SEQUENCE: 154
tgtaaaggat gatgtggtgg ta                                                 22

<210> SEQ ID NO 155
<211> LENGTH: 21
<212> TYPE: DNA
<213> ORGANISM: Artificial Sequence
<220> FEATURE:
<223> OTHER INFORMATION: synthetic

<400> SEQUENCE: 155
aagtatggaa ggtagtaggg t                                                  21
```

MIRNAS INVOLVED IN THE BLOOD BRAIN BARRIER FUNCTION

BACKGROUND

The blood-brain barrier (BBB) separates the blood and the central nervous system (CNS). The central nervous system consists of the brain and the spinal cord. This separation between the blood and CNS is created by specialized endothelial cells, brain endothelial cells, which are distinct from peripheral endothelial cells, as the blood-brain barrier is composed of high density cells restricting passage of substances from the bloodstream much more than endothelial cells elsewhere in the body (Abbott et al., Nat Rev Neurosc, 2006, 7, 41-53). The BBB restricts the diffusion of large or hydrophilic molecules into the CNS, e.g. antibodies, but also of microscopic entities, e.g. bacteria. On the other hand, small hydrophobic molecules, e.g. hormones and oxygen, can diffuse over the BBB. The BBB also actively transports molecules, such as for instance glucose, across the BBB utilizing transporter proteins. Cells of the immune system can also pass the BBB (Pachter et al., J Neuropathol Exp Neurol. 2003 June; 62(6):593-604; Abbott et al., Nat Rev Neurosc, 2006, 7, 41-53; Begley and Brightman, Prog Drug Res. 2003; 61:39-78; Loscher and Potschka, NeuroRx. 2005 January; 2(1):86-98; Carvey et al., Neurochem. 2009 October; 111(2):291-314; Abbott et al., Neurobiol Dis. 2010 January; 37(1):13-25). In summary, the function of the BBB is to allow precise control over the substances that leave or enter the central nervous system, and this function is essential for brain homeostasis and reliable functioning of the neuronal environment.

A common feature of diverse brain abnormalities such as for example multiple sclerosis, brain cancer, Alzheimer's disease, stroke, epilepsy and traumatic brain injury, is reduction or loss of the specialized function of the BBB, leading to unstable brain homeostasis and neuronal damage (Zlokovic, Neuron. 2008 Jan. 24; 57(2):178-201; Friedman et al., Epilepsy Res. 2009 August; 85(2-3):142-9; Carvey et al., Neurochem. 2009 October; 111(2):291-314; Abbott et al., Neurobiol Dis. 2010 January; 37(1):13-25).

On the other hand, in brain abnormalities in which the BBB function is maintained, the BBB can obstruct or hamper the entry of pharmaceuticals or drugs. For instance, many high potential drugs for the central nervous system (CNS), for instance biopharmaceuticals such as antibodies, are currently not or less suitable for use in the treatment of the CNS because these drugs can often not cross the blood-brain barrier, making the BBB a major hurdle for successful CNS drug development that require drugs to pass the BBB.

Current strategies for drug delivery in the brain involve invasive measures such as for instance stereotactic injections in the brain or intrathecal injections, which both means the BBB is physically disrupted and which always involves a risk of neural injuries. Other means include disruption of the BBB by osmotic means, or biochemically by the use of vasoactive substances such as bradykinin or even by localized exposure to high intensity focused ultrasound (HIFU), but success has been limited (Daffertshofer and Fatar, Eur J. Ultrasound. 2002 November; 16(1-2):121-30; Doolittle et al., J Neurosci Nurs. 1998 April; 30(2):81-90; Wahl et al., Acta Physiol Hung. 1999; 86(2):155-60). As such, there remains a need for methods and compounds that can safely and effectively modulate, i.e. increase or decrease the blood brain barrier function. With an increase of the blood brain barrier function is meant that the blood brain barrier becomes less permeable for the passive transfer of compounds across the BBB, for example (therapeutic) antibodies or antibiotics. With a decrease of the blood brain barrier function is meant that the blood brain barrier becomes more permeable for the passive transfer of compounds such as for example (therapeutic) antibodies or antibiotics across the BBB. Such compounds or methods that would influence the BBB function would be beneficial, as for instance co-administration of a compound that decreases the blood brain barrier with a drug, e.g. therapeutic antibodies or antibiotics, that normally is less capable or incapable of passing the BBB might result in the improved delivery of said drug to the brain. In addition, a compound that increases the blood brain barrier function may allow the (partial) reconstitution of the blood brain barrier function in patients that suffer from impaired BBB function. An increase of the BBB function might for instance prevent bacterial infiltration of the brain or reduce seizures, or help to restore homeostasis.

Unfortunately, the discovery of compounds that may modulate the BBB has been hampered by a lack of understanding of the functioning of the BBB and the pathways involved, as well by the absence of easy methods to determine BBB function. For instance, in vivo animal knockout models were used in which the involvement of certain transmembrane proteins involved in the BBB function such as for instance the G protein-coupled receptor 124 was observed (GPR124) (WO2008147528). Downregulating GPR124 with an antagonist was suggested to decrease the BBB function. On the other hand, increasing expression of GPR124 may provide for increased BBB function. In addition, it has also been suggested that inhibiting claudin-5 expression using RNA interference with hydrodynamic tail vein injections may be used to "open up" the BBB (WO2009047362). In such animal experiments the permeability of the BBB is determined by measuring the uptake by the brain of tracer molecules that normally have difficulty or can not pass the BBB. Obviously, in vivo animal models or knock-out studies do not allow large scale screening for new candidate compounds.

A less complicated assay to study the BBB function is an in vitro assay in which (primary) brain endothelial cells are cultured in vitro on a membrane and passage of tracer compounds through the membrane is determined. Alternatively, the electrical resistance (expressed as ohm) over the cultured brain endothelial cells can also be measured, i.e. the transendothelial electric resistance (Deli et al., Cell Mol. Neurobiol. 2005 February; 25(1):59-127). Importantly, in many of these in vitro assays the cells have to be grown to full confluency in order to ensure that the tracer compounds (or current) has to pass the brain endothelial cell layer and does not simply bypass the membrane without encountering the brain endothelial cells. Although these in vitro models are a major improvement over the in vivo experiments, they are laborious and technically challenging, making large scale screening to identify compounds that influence BBB function still a very difficult task.

In summary, a problem in the development of a medical treatment for the central nervous system, e.g. the brain, is that there is a need for compounds that can safely and effectively modulate, i.e. increase or decrease, the blood brain barrier function. In addition, there is a need for assays that are robust and simple to perform to allow for large scale screening for compounds (or compound libraries) that can modulate the blood brain barrier function.

SUMMARY OF THE INVENTION

The present invention now surprisingly solves at least one of the problems as described above. In the current invention it was found for the first time that particular nucleic acids, including those listed in SEQ ID No. 1-152, play an important role in modulating the BBB function. As can be witnessed in detail from the examples, it was found that the nucleic acids according to the invention, and including those selected from the group consisting of SEQ ID No. 1-152, are capable of modulating, in particular increasing the blood brain barrier function.

Furthermore, blocking said nucleic acids, including those selected from the group consisting of SEQ ID No. 1-152, results in a decrease in the blood brain barrier function as described for instance in example 4. In the current invention, blocking of a nucleic acid is achieved by providing a (partially) complementary nucleic acid sequence that can (partially) hybridise to the nucleic acid, such that when the (partially) complementary nucleic acid sequence is hybridised with the nucleic acid (and thus bound thereto), the nucleic acid can not perform its function, e.g. hybridizing with a target molecule, i.e. it is blocked.

Finally, the relative expression level of the nucleic acids according to the invention, including those listed in SEQ ID No. 1-152 can be used as a measure/indicator of blood brain barrier function. For instance, when the expression level of a particular level of a nucleic acid is increased, relative to a control setting, the BBB function is increased. Alternatively, when the expression level of a particular level of a nucleic acid is decreased, relative to a control setting, the BBB function is decreased. Such an increase or decrease of the level of expression of a nucleic acid may be induced by the presence of a compound. Thus, the invention further provides for an assay (method) for screening for compounds or compound libraries to identify compounds that are capable of modulating BBB function. The assay comprises of determining the expression level(s) of at least one nucleic acid sequence as listed in SEQ ID No. 1-152 in the absence and/or presence of a compound to be tested.

DEFINITIONS

Figure 1:
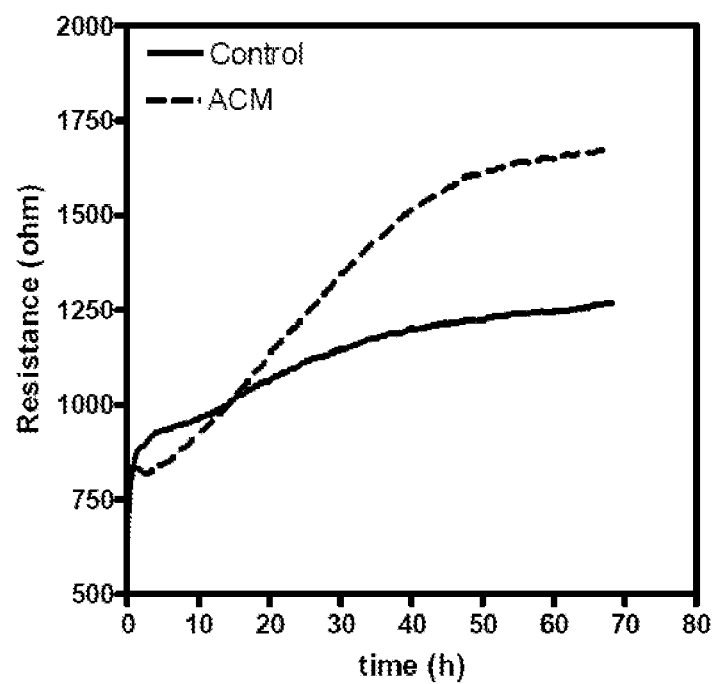
FIG. 1 is a graph of transendothelial electrical resistance (TEER) measurements of endothelial brain cells in a culture medium with astrocyte conditioned medium (ACM) or without (control) at 70 hours post-seeding.

In the description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

As used herein, the singular forms "a," "an" and "the" include plural referents unless the context clearly dictates otherwise. For example, "a" nucleic acid as mentioned below, includes a plurality of molecules (e.g. 10's, 100's, 1000's, 10's of thousands, 100's of thousands, millions, or more molecules).

A nucleic acid or a nucleic acid sequence according to the present invention may include any polymer or oligomer of pyrimidine and purine bases, preferably cytosine, thymine, and uracil, and adenine and guanine, respectively (See Albert L. Lehninger, Principles of Biochemistry, at 793-800 (Worth Pub. 1982)). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In other embodiments a nucleic acid or nucleic acid sequence of the invention comprises other kinds of nucleic acid structures such as for instance a DNA/RNA helix, peptide nucleic acid (PNA), morpholino, locked nucleic acid (LNA) and/or a ribozyme. Hence, the term "nucleic acid" or "nucleic acid sequence" may also encompass a chain comprising non-natural nucleotides, modified nucleotides and/or non-nucleotide building blocks which can exhibit the same function as natural nucleotides. As used herein, such non-natural nucleotides, modified nucleotides and/or non-nucleotide building blocks are referred to with the term "nucleotide analogues".

The term "% sequence identity" is defined herein as the percentage of nucleotides or nucleotide analogues in a nucleic acid sequence according to the invention that is identical with the corresponding nucleotides in a reference sequence after aligning the two sequences and introducing gaps, if necessary, to achieve the maximum percent identity. Hence, in case a nucleic acid according to the invention is longer than a reference sequence, additional nucleotides in the nucleic acid according to the invention, that do not align with the reference sequence, are not taken into account for determining sequence identity. Methods and computer programs for alignment are well known in the art. One computer program which may be used or adapted for determining the percentage of sequence identity is "Align 2", authored by Genentech, Inc., which was filed with user documentation in the United States Copyright Office, Washington, D.C. 20559, on Dec. 10, 1991.

The term "complementarity" is defined herein as nucleotides of a nucleic acid sequence that can bind to another nucleic acid sequence through hydrogen bonds, i.e. nucleotides that are capable of base pairing. Nucleotides that can form base pairs, that are complementary to one another, are e.g. cytosine and guanine, thymine and adenine, adenine and uracil, guanine and uracil. The percentage complementarity does not have to be calculated over the entire length of a nucleic acid sequence. The percentage of complementarity may be limited to a specific region of which the nucleic acid sequences which are base-pared, e.g. starting from a first base-paired nucleotide and ending at a last base-paired nucleotide. For example, and in an embodiment according to the current invention, a nucleic acid may comprise a nucleic acid sequence of which at least 8 adjacent nucleotides are at least 75% complementary to 8 adjacent nucleotides of the complementary nucleic acid that may comprise 8 nucleotides, 16 nucleotides, or 32 nucleotides, or more. As long as of 8 adjacent nucleotides of the nucleic acid sequence at least 6 nucleotides can base-pair with 8 adjacent nucleotides of the complementary nucleic acid sequence the nucleic acid sequence is at least 75% complementary. The term comprises according to the invention is to be interpreted such that for example a nucleic acid comprising a nucleic acid sequence of 8 adjacent nucleotides may also include a nucleic acid consisting of no more than said 8 adjacent nucleotides.

The term "gene expression" as used throughout, is defined as RNA transcription of a gene, e.g. expression of mRNA, and/or translation of mRNA into protein. Gene expression thus comprises RNA expression and/or protein expression. For example, miRNA genes may express RNA transcripts that are subsequently processed by the miRNA machinery. For a miRNA gene, gene expression thus comprises the transcript that is initially transcribed, the subsequent intermediate processed transcripts, and finally the miRNA molecule which may be incorporated in the RISC complex. Furthermore, gene expression of a gene encoding a protein comprises the initially transcribed RNA molecule, but may also comprise subsequently spliced or otherwise by the cellular machinery processed transcribed RNA molecules, and/or the protein which may be translated from messenger RNA (mRNA).

When reference is made to the "expression level" of a gene, the expression level is to be understood as the amount of RNA transcript that is transcribed by a gene and/or the amount of protein that may be translated from an RNA transcript, e.g. mRNA. For example, for genes which encode a miRNA, the expression level may be determined through quantifying the amount of RNA transcript which is expressed, e.g. using standard methods such as quantitative PCR of a mature miRNA, microarray, or Northern blot. Alternatively, the expression level may also be determined through measuring the effect of a miRNA on a target mRNA. For example, a 3'UTR sequence comprising a target miRNA target sequence may be incorporated in a reporter gene, e.g. luciferase, this way, the expression level of a miRNA gene may be indirectly measured by measuring the amount of Luciferase expression which may be controlled by a particular miRNA. Furthermore, in case the 3'UTR sequence is from a particular gene, the amount of Luciferase expression also correlates with the expression level of the particular gene. As such, when determining the expression level of a miRNA as described above (e.g. directly through qPCR or indirectly with a reporter gene construct), in addition, the expression level of the miRNA may be correlated to the expression level of a target gene of the particular miRNA. The amount of protein that may be translated from an RNA transcript may also be measured to determine the expression level of a gene. Methods are known in the art, such as ELISA and Western blot. Alternatively, the expression level of a protein may also be indirectly measured. For example, in case the expression level of an RNA transcription factor needs to be determined, a reporter gene construct may be used which comprises the RNA transcription factor binding site. The expression level may than be subsequently determined by measuring the reporter gene construct expression, e.g. in case GFP is used, green fluorescence intensity may be determined as a measure of the expression level of the RNA transcription factor.

DETAILED DESCRIPTION OF THE INVENTION

In a first aspect of the invention there is provided for the use a nucleic acid comprising a nucleic acid sequence which has at least 70%, preferably 75%, more preferably 80%, even more preferably 85%, even more preferably 90%, even more preferably 95%, most preferably 100% sequence identity with a nucleic acid sequence selected from the group consisting of SEQ ID No 1-152, for increasing blood-brain barrier function. For instance, said nucleic acids may be used in vitro or in vivo for modulating the blood brain barrier function. With in vivo is meant for instance in an animal model or a patient, with in vitro is meant a (primary) cell culture. The nucleic acids may be provided in the cell, for instance via transfection or other means of cell transfer, as explained below. A nucleic acid according to the invention for example can comprise a nucleic acid sequence which has 95% sequence identity with SEQ ID No. 10 (miR-27a). Such a nucleic acid can be 21 nucleotides, the exact length of SEQ ID No. 10, 30 nucleotides, or can be 50 nucleotides. If said nucleic acid is 50 nucleotides, it comprises a nucleic acid sequence that aligns with the nucleic acid sequence of SEQ ID No.10. As the nucleic acid sequence has 95% identity with SEQ ID No. 10, which is 21 nucleotides, of said nucleic acid sequence, 20 nucleotides correspond to nucleotides of SEQ ID No.10. In addition, there is provided for a nucleic acid comprising a nucleic acid sequence which has at least 70%, 75%, 80%, 85%, 90%, 95%, 100% sequence identity with a nucleic acid sequence selected from the group of SEQ ID No 1-152, wherein the nucleic acid is not a nucleic acid selected from the group of SEQ ID No 1-152.

The blood-brain barrier function according to the invention can, for example, be measured by determining the transendothelial electric resistance (TEER) of an endothelial brain cell monolayer, as is described in detail in Example 1. TEER is expressed in ohm. For instance, the ECIS™ Model 1600R (Applied BioPhysics, Troy, N.Y., USA) can be used to measure the TEER according to the manufacturers instructions. By measuring TEER the resistance of an endothelial brain cell monolayer to an electric current is measured, i.e. the ion permeability of the endothelial brain cell monolayer. A relative high resistance means that less ions, and thus less current, can permeate the endothelial brain cell monolayer, a relative low resistance means that more ions, and thus more current, can pass through the endothelial brain cell monolayer. Ion permeability of the endothelial brain cell monolayer correlates with the ability of compounds to passively diffuse across the blood brain barrier. Thus, the TEER value measured relates to the BBB function. Within the context of the current invention, increasing the blood-brain barrier function means that relative to a control setting, the TEER is increased when measured in the method described. Also, decreasing the blood-brain barrier function means that relative to a control setting, the TEER is decreased when measured in the method described. A control setting is defined as a setting in which certain conditions (e.g. salt, nutrient and biological factor concentrations, pH, temperature etc.) are selected. For instance, conditions may be selected that most closely resemble the conditions of a healthy patient, but for instance conditions may also be selected such as may occur in a diseased or injured patient in which BBB function is known to be disturbed. Whichever conditions selected, in the control setting the TEER is measured. Next, in a different setting comprising e.g. a composition for increasing or decreasing the blood-brain barrier function, the TEER is determined. In this different setting similar conditions are selected as in the control setting, but now a composition or compound is added that can, for instance, increase the BBB function. When comparing the TEER resistance value (ohm) for the latter condition, relative to the control setting, the TEER will have increased, i.e. having a higher value and thus a higher resistance, meaning that less ions, and thus less compounds, can pass through the endothelial cell layer, and the BBB function has increased. The BBB function as defined is within the context of the assay. An increase or decrease of the BBB function within the assay indicates that in alternative settings wherein the blood brain barrier is studied, e.g. in in vivo, or in vivo models, or in a therapeutic setting the blood brain barrier may have a similar effect and result in an increase or decrease of the blood brain barrier function in these settings.

Surprisingly it was found that, when comparing (control vs. ACM) the expression level of putative miRNA sequences, a selection of putative miRNA sequences was at least two-fold upregulated in the blood-brain barrier, i.e. in brain-endothelial cells, see Example 2 and SEQ ID No. 1-152. Furthermore, it was found that an increase in the expression of said nucleic acid sequences in the blood brain barrier, i.e. in brain endothelial cells, was found to result in an increase in the BBB function. Support for the involvement of putative miRNA sequences in the BBB function was further provided as it was found that knocking down an essential factor from the miRNA biogenesis pathway, the DICER enzyme (Winter et al., Nature Cell Biol 2009, vol 11, nr 3, p. 228-234), resulted in a decrease in BBB function (example 3). Thus, the miRNA biogenesis pathway, and consequently, miRNA function is implicated in BBB function.

With respect to these putative miRNA's, the discovery of miRNAs, a new class of endogenous small non-coding RNAs, has dramatically changed the perspective on gene regulation. With non-coding RNAs is meant RNAs that do not encode for a protein, i.e. are not translated into a protein such as coding RNAs, e.g mRNA. Without being bound by theory, it is the inventors' belief that these small non-coding RNAs according to the invention may be involved in the regulation of gene expression and are activated through incorporation into an enzyme complex called the RNA-induced silencing complex (RISC), via the RNA interference pathway. Protein expression is thought to be regulated through (partial) complementary base-pairing of the putative miRNA with target sequences in the 3' untranslated region of target mRNA, thereby causing degradation of the mRNA and/or translational repression, leading to improved BBB function. These putative miRNAs may also possibly act via transcriptional gene silencing or even activation of transcription and/or translation as this has also been occasionally described for (putative) miRNA sequences (Morris, Biotechniques. 2006 April; Suppl:7-13; Chua et al., Curr Opin Mol. Ther. 2009 April; 11(2):189-99). These other possible mechanisms all can depend on base-pairing of a putative miRNAs with for instance chromosomal DNA, thereby inducing chromatin remodelling that can result in transcriptional activation or silencing. A (putative) miRNA can also interact with a messenger RNA in order to stabilize it thereby preventing degradation and/or processing. Furthermore, other modes of activity of the putative miRNA sequences according to the invention, and leading to improved BBB functioning are not excluded by the invention. Hence, the term miRNA activity includes the modes of activity as described above.

Thus, according to the invention, there is provided for use of a nucleic acid comprising a nucleic acid sequence which has at least 70%, preferably 75%, more preferably 80%, even more preferably 85%, even more preferably 90%, even more preferably 95%, most preferably 100% sequence identity with a nucleic acid sequence selected from the group consisting of SEQ ID No 1-152, for increasing blood-brain barrier function. In addition, there is provided for a nucleic acid comprising a nucleic acid sequence which has at least 70%, preferably 75%, more preferably 80%, even more preferably 85%, even more preferably 90%, even more preferably 95%, most preferably 100% sequence identity with a nucleic acid sequence selected from the group consisting of SEQ ID No 1-152, wherein said nucleic acid is not a nucleic acid selected from the group consisting of SEQ ID No. 1-152. These nucleic acids or use thereof according to the invention have been found to be particular advantageous for increasing the blood-brain barrier function, for example as determined according to the methods disclosed in the Examples.

The skilled person is well capable to determine whether a nucleic acid according to the invention increases the BBB function. For instance, a nucleic acid according to the invention can be transfected or transduced into a brain endothelial cell as described in example 3 and 4, and the effect on the TEER can be measured. It is to be understood that the term comprising within the context of the above is meant to also include a nucleic acid according to the invention consisting of the nucleic acid sequence having 70%, 75%, 80%, 85%, 90%, 95%, or 100% sequence identity with a nucleic acid sequence selected from the group consisting of SEQ ID No. 1-152. Thus, the nucleic acid sequence which comprises a nucleic acid sequence having 70%, 75%, 80%, 85%, 90%, 95%, or 100% sequence identity with a nucleic acid sequence selected from the group consisting of SEQ ID No. 1-152, can consist of the same number of nucleotides of a nucleic acid sequence from SEQ ID No. 1-152, but may also comprise additional nucleotides, for instance 1, 2, 3, 4, 5, 6, 7, 8, 9, 10, 20, 100 nucleotides, or any other integer, as long as the nucleic acid according to the invention is capable of increasing the BBB function. Furthermore, the nucleic acid may also consist of a fragment of a sequence according to SEQ ID No. 1-152, such a fragment may be for instance as small as 10 nucleotides, although the fragment may be larger or smaller, as long as the fragment is capable of increasing the BBB function, as can be determined according to the methods provided by the invention. Furthermore, preferably a nucleic acid according to the invention comprises a nucleic acid sequence which has at least 70%, preferably 75%, more preferably 80%, even more preferably 85%, even more preferably 90%, even more preferably 95%, most preferably 100% sequence identity with a nucleic acid sequence selected from the group consisting of SEQ ID No 1-152, for increasing blood-brain barrier function, wherein said nucleic acid is not a nucleic acid sequence selected from the group consisting of SEQ ID No 1-152.

Preferably, a nucleic acid or the use thereof according to the invention as disclosed above, preferably comprises a nucleic acid sequence with a sequence identity as disclosed above with a nucleic acid sequence selected from the group consisting of SEQ ID No. 1-120, more preferably from the group consisting of SEQ ID No. 1-100, most preferably from the group consisting of SEQ ID No. 1-80, as these preferentially selected sequences have at least a 2.41, 2.59, and 2.90 fold increase in expression respectively when the BBB function is increased, see example 1 and 2. The higher the fold increase in expression of a sequence as listed in SEQ ID No 1-152, the stronger the effect on the BBB function may be. Thus, according to this embodiment, a nucleic acid sequence as selected from the group of SEQ ID No. 1-152 preferably has a high fold increase of expression. Alternatively, it is therefore preferred that a nucleic acid or the use thereof according to the invention comprises a nucleic acid sequence with a sequence identity as disclosed above with a nucleic acid sequence having a fold induction of at least 2.50, preferably at least 3.00, more preferably at least 3.50, even more preferably at least 4.00, most preferably at least 4.50, as shown in Table1.

Figure 5:
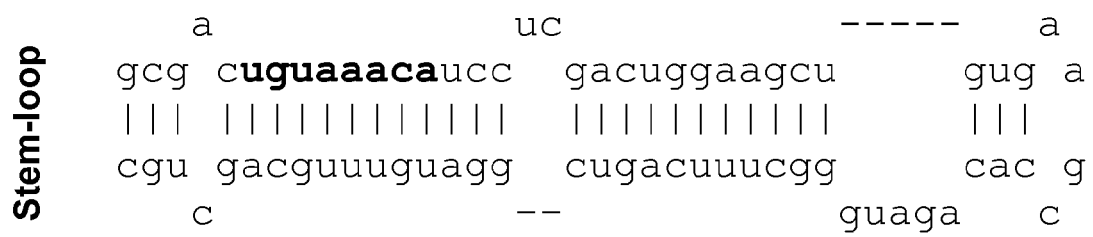
FIG. 5 shows a stem-loop structure (SEQ ID NO: 153) and the seed sequence of miR-30 family.

Yet more preferably, a nucleic acid or the use thereof according to the invention as disclosed above, preferably comprises a nucleic acid sequence with a sequence identity as disclosed above with a nucleic acid sequence belonging to the miR-30 family, preferably selected from the group consisting of SEQ ID No 32, SEQ ID No 37, SEQ ID No 38, SEQ ID No 53 and SEQ ID No 80. These nucleic acid sequence have at least a 2.90-fold increase in expression when the BBB function is increased, see example 1 and 2, and in addition were found to show a decrease in expression when the BBB function is decreased, which is indicative of their strong effect on BBB function. SEQ ID No 32, SEQ ID No 37, SEQ ID No 38, SEQ ID No 53, SEQ ID No 80, belonging to the miR-30 family, have a common feature in that they comprise 11 identical bases at one end: UGUAAACAUCC corresponding to nucleotides 6-13 of SEQ ID NO:153 (see FIG. 5).

In a preferred embodiment, the nucleic acid, as described above, comprising a nucleic acid sequence which has at least 70%, 80%, 85%, 90%, 95%, or 100% sequence identity with a nucleic acid sequence selected from the group of SEQ ID No 1-152 is a pre-miRNA, a pri-miRNA, a siRNA or a shRNA. Without being bound by any theory, the sequences as listed, are in the art referred to as microRNA or miRNA sequences (Bartel D. P. (2004) Cell 116, 281-297). miRNAs are a novel class of endogenous small non-coding RNAs, which are believed to regulate gene expression via the so-called RNA interference pathway (RNAi). The primary transcripts of miRNAs can be transcribed by RNA polymerase II and III which generally have a length of several kilobases, and are called primary miRNAs (pri-miRNA). A typical animal pri-miRNA comprises an imperfectly paired stem of 30-35 bp, with a terminal loop and flanking segments (Bartel (2004) Cell 116, 281-297). These pri-miRNAs, which are capped and polyadenylated (Kim (2005) Nature Rev. Mol. Cell. Biol. 6 376-385), are subsequently processed by the miRNA biogenesis pathway (reviewed in Winter et al., Nature Cell Biol 2009, vol 11, nr 3, p. 228-234), in the cell nucleus to shorter, 70-100 nucleotide stem-loop structures known as pre-miRNAs. This processing can be performed in animals by the RNase III endonuclease Drosha. Pre-miRNAs can subsequently be transported into the cytoplasm by exportin-5, where they can be processed to double-stranded miRNAs, a miRNA duplex, with a length of 21-25 nucleotides by the RNase III endonuclease DICER. The miRNA duplex comprises the miRNA nucleic acid sequence, which may be subsequently incorporated into the RNA-induced silencing complex (RISC). When the miRNA is incorporated into RISC, this activated RISC complex, i.e. a RISC complex loaded with a miRNA, can inhibit gene expression of a target gene by inhibiting translation and/or by cleaving mRNA through complementary base-pairing, although other regulatory mechanisms can be envisaged as disclosed above. One of the key differences between miRNAs and most siRNAs (small interfering RNA) is that most species of a miRNA have a highly conserved end, although there is variation (Carthew and Sontheimer (2009) Cell 136, 642-655). For example, such highly conserved end consists of 5-9 bases that are identical within a species of a miRNA. In contrast, siRNAs tend to be much more heterogeneous in end composition.

As the nucleic acid sequences of SEQ ID No 1-152 may represent human miRNA sequences, the pre-miRNA or pri-miRNA according to the invention may comprise the natural sequences from which such a miRNA is processed, i.e. the endogenous sequence as it is expressed in nature. However, non-natural nucleic acid sequences, i.e. exogenous artificial pre-miRNA, pri-miRNA or a miRNA duplex RNA structures are also possible (Aagaard et al., Gene Ther. 2008 December; 15(23):1536-49; Liu et al., Nucleic Acids Res. 2008 May; 36(9):2811-24). In that respect, it is also be possible to incorporate the nucleic acid sequences according to the invention in so-called small interfering RNA (siRNA) (Elbashir et al., Nature. 2001 May 24; 411(6836):494-8) or short hairpin RNA (shRNA) (Brummelkamp et al., 2002 Apr. 19; 296 (5567):550-3). A short hairpin RNA can comprise two short complementary RNA sequences of 19-35 nucleotides long with a loop sequence in between such that a hairpin structure can be formed. A small interfering RNA may comprise two complementary strands of 19-25 nucleotides. A shRNA may also be processed by the RNA interference pathway, by the DICER enzyme, resulting in an siRNA. As with a duplex miRNA, one of the strands of the siRNA duplex has been suggested to be incorporated into RISC, resulting in an activated RISC complex. Thus, a nucleic acid comprising a nucleic acid sequence which has at least 70%, 80%, 85%, 90%, 95%, 100% sequence identity with a nucleic acid sequence selected from the group of SEQ ID No 1-152, is preferably a pre-miRNA, pri-miRNA, siRNA, shRNA, or is hybridised to a complement nucleic acid sequence thus forming a siRNA duplex or miRNA duplex, such that the nucleic acid sequence with at least 70%, 80%, 85%, 90%, 95%, 100% sequence identity with a nucleic acid sequence selected from the group of SEQ ID No. 1-152 is compatible with the RNA interference pathway. Thus, according to this embodiment, the provided nucleic acid may be recognized and processed by the RNA interference pathway or miRNA biogenesis pathway (Winter et al., Nature Cell Biol 2009, vol 11, nr 3, p. 228-234) such that the nucleic acid sequence which has at least 70%, 80%, 85%, 90%, 95%, 100% sequence identity with a nucleic acid sequence selected from the group of SEQ ID No 1-152 can have its action for increasing the blood-brain barrier function.

In a further embodiment, a nucleic acid according to the invention as disclosed above, is for use in a treatment for increasing blood-brain barrier function. It has been found that in particular these nucleic acids can advantageously be used to increase the blood-brain barrier function. In particular, such a treatment may be a medical treatment of a patient suffering from a neurological condition. For instance, for many neurological conditions, BBB damage is an early event, and thus increasing BBB function as an early intervention for treating such conditions may slow down, stop or even reverse such neurological conditions. Preferably, a nucleic acid according to the invention as disclosed above is for use in treatment of stroke, brain trauma, infection, inflammation, multiple sclerosis, HIV infection, Alzheimer's disease, Parkinson's disease, epilepsy, brain tumours, glaucoma, lysosomal storage diseases, prion disease, retinal dysfunction, cerebrovascular disease, migraine and peroxisome-associated diseases. In these conditions, the blood brain barrier function is compromised leading to unstable brain homeostasis and neuronal damage (Zlokovic, Neuron. 2008 Jan. 24; 57(2): 178-201 and Abbott et al., Neurobiol Dis. 2010 January; 37(1):13-25). In such diseases it may be beneficial to provide patients with a treatment that may increase the blood-brain barrier such that homeostasis may be (partially) restored and neuronal damage reduced. It is to be noted that the use of a single nucleic acid according to the invention may suffice for increasing the blood-brain barrier function, however, it is also well within the scope of the invention to combine multiple nucleic acids according to the invention such that an enhanced effect for increasing the blood-brain barrier is obtained. Thus, the invention provides for the use of at least one nucleic acid according to the invention as described above, for use in a medical treatment, in particular for increasing the BBB function in a patient. In particular, conditions such as disclosed above are treated, as patients suffering from these conditions would benefit from increasing the BBB function, but other conditions in which a patient may benefit from an increase of BBB function may also be included.

According to another aspect of the current invention, there is provided for nucleic acids, and the use thereof, that can bind, hybridize and/or base-pair to a nucleic acid comprising a nucleic acid sequence selected from the group consisting of SEQ ID No 1-152, thereby blocking the function thereof, for decreasing the blood brain barrier function according to the invention. Preferably such a nucleic acid binds, hybridizes and/or base-pairs (i.e. forms base pairs) with (part of) the a nucleic acid that comprises or consists of a nucleic acid sequence selected from the group consisting of SEQ ID No 1-152. Such blocking nucleic acids are also known in the art for instance as antagomirs (Krützfeldt et al., Nature, 2005 Dec. 1; 438(7068):685-9).

In a further embodiment a nucleic acid is provided comprising a nucleic acid sequence of which at least 8 adjacent nucleotides are at least 70%, preferably 75%, more preferably 80%, even more preferably 85%, even more preferably 90%, even more preferably 95%, most preferably 100% complementary to 8 adjacent nucleotides of a nucleic acid sequence selected from the group of SEQ ID No 1-152. In other words, such nucleic acid has 4, 5, 6, 7, or 8 adjacent nucleotides that are complementary to 8 adjacent nucleotides of a nucleic acid sequence from the group of SEQ ID No 1-152. These nucleic acids can in particular be used for decreasing the blood brain barrier function. For example, a nucleic acid according to this embodiment exactly 8 nucleotides, or 16 nucleotides, or 30 nucleotides in size, or even larger, and said nucleic acid comprises a nucleic acid sequence of 8 nucleotides that are (partially) complementary to a nucleic acid from the group of SEQ ID No. 1-152. In case the nucleic acid is longer than 8 nucleotides, the additional nucleotides do not necessarily have to base pair, i.e. be complementary, with the nucleic acid sequence from SEQ ID No. 1-152.

Figure 4:
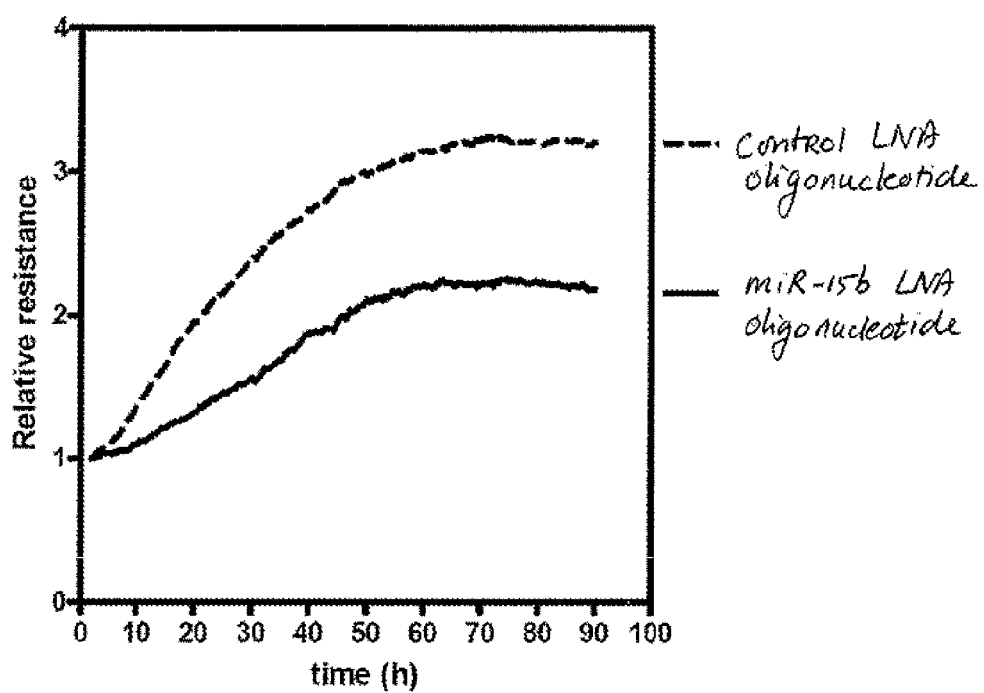
FIG. 4 is a graph of the relative resistance (in terms of TEER) of endothelial brains cells transfected with either miR-15b LNA oligonucleotide or control LNA oligonucleotide at 48 hours post-transfection relative to 0 hours (where relative resistance is set at 1).

Likewise there is provided for the use of such a nucleic acid comprising a nucleic acid sequence of which at least 8 adjacent nucleotides are at least 70%, preferably 75%, more preferably 80%, even more preferably 85%, even more preferably 90%, even more preferably 95%, most preferably 100% complementary to 8 adjacent nucleotides of a nucleic acid sequence selected from the group of SEQ ID No. 1-152, for decreasing blood-brain barrier function. Such nucleic acid is capable of binding to a nucleic acid comprising a nucleic sequence selected from the group of SEQ ID No. 1-152, to thereby block a nucleic acid comprising a nucleic acid sequence selected from the group of SEQ ID No 1-152. The term blocking herewith is being defined as preventing the nucleic acid sequence of SEQ ID No. 1-152 from performing its function as described herein, e.g. having a miRNA activity or increasing the BBB function. As nucleic acid sequences from the group of SEQ ID No. 1-152 are involved in the BBB function, i.e. an increased concentration of said nucleic acid comprising said nucleic acid sequences results in an increased BBB function, blocking the said nucleic acid sequences with a complementary nucleic acid sequence has been found to block its normal function, e.g. may be used for decreasing the BBB function. Thus, as a nucleic acid comprising a nucleic acid sequence selected from the group consisting of SEQ ID No 1-152 is involved in maintaining or increasing BBB function, blocking a nucleic acid comprising a nucleic acid sequence selected from the group of SEQ ID No 1-152 may result in a decrease of BBB function. A decrease in BBB function means that relative to a control, the TEER is decreased. For instance, in a control setting the TEER is measured. Next, in a different setting, comprising e.g. a nucleic acid for decreasing the blood-brain barrier function, the TEER is determined. When comparing the TEER resistance value (ohm) for the latter condition, relative to the control setting, the TEER has been decreased, i.e. having a lower value and thus a lower resistance. The skilled person is aware of methods in the art to determine whether a nucleic acid according to the above embodiment is capable of blocking the complementary nucleic acid sequence selected from the group of SEQ ID No 1-152. This can for example be determined in analogy with Example 4, where it is described that blocking in particular miR-15b reduces the BBB function (FIG. 4). Other putative miRNAs, as listed in SEQ ID No. 1-152, according to the invention may be blocked similarly with similar decreasing effects on the blood brain barrier function (FIG. 4).

In an another embodiment, there is provided that the nucleic acid comprising a nucleic acid sequence of which at least 8 adjacent nucleotides are at least 85%, most preferably 100% complementary to 8 adjacent nucleotides of a nucleic acid sequence selected from the group of SEQ ID No 1-152 for decreasing the blood brain-brain barrier function further comprises nucleotide analogues. Nucleotide analogous, such as for instance Locked Nucleic Acids (Chan et al., Clin Exp Pharmacol Physiol. 2006 May-June; 33(5-6):533-40) as used in example 4, are in particular advantageous as nucleotide analogous can increase the stability of the nucleic acids, i.e. they may provide resistance to nucleases, but can also increase the strength of the complementary base-pairing (binding affinity) between the nucleic acid sequence and the target sequence, i.e. a nucleic acid sequence selected from the group of SEQ ID No 1-152. As long as the nucleic acid sequence comprising the nucleotide analogue is capable of complementary base-pairing with its target sequence and/or reducing the blood brain barrier function, the skilled person may select such analogues, however, it is preferred to select analogues that result in an improvement of the stability and/or binding affinity. Other nucleotide analogues are well known in the art, such as for instance morpholinos (Summerton and Weller Antisense Nucleic Acid Drug Dev. 1997 June; 7(3): 187-95). Accordingly, (a) nucleotide analogue(s) may result in an increased stability of the nucleic acid, and may improve the binding of the nucleic acid to its target, thereby improving its capacity to block its target, i.e. improving the blocking of a nucleic acid sequence selected from the group of SEQ ID No 1-152, for decreasing the blood brain-brain barrier function./esp In a further embodiment, the nucleic acid provided comprising a nucleic acid sequence of which at least 8 adjacent nucleotides are at least 85%, most preferably 100% complementary to 8 adjacent nucleotides of a nucleic acid sequence selected from the group of SEQ ID No 1-152 for decreasing the blood-brain barrier function, which may further comprise nucleotide analogues, is for use in a treatment, for example a medical treatment, for decreasing the blood-brain barrier function. Preferably, such a nucleic acid is for use in treatment of infection, inflammation, multiple sclerosis, HIV infection, Alzheimer's disease, Parkinson's disease, epilepsy, brain tumours, glaucoma, lysosomal storage diseases, prion disease, retinal dysfunction, cerebrovascular disease, migraine or peroxisome-associated diseases. For instance, it is known in the art that polyoma viruses, e.g. JCV, HIV-1, or Japanese encephalitis virus may passage through the blood brain barrier. By decreasing the BBB function, the viral infiltration of the CNS may be more effectively treated with antiviral medication, as the antiviral medicine may more easily penetrate the brain to have its action. Similarly, in the above neurological conditions, it may be beneficial in a relatively early stage of disease to decrease the blood brain barrier function, such that the brain may become accessible to pharmaceuticals that would otherwise not be effective. For instance, in case of brain cancer with still an intact blood brain barrier, it may be beneficial to treat a patient with an anti-cancer drug, e.g. a specific antibody, in combination with a nucleic acid according to the invention for reducing the BBB function. By combining the drug with the nucleic acid according to the invention for reducing the BBB function, the anti-cancer drug may now effectively reach the brain cancer. Accordingly, such a treatment preferably further comprises the use of a medicament that would benefit from decreasing the blood-brain barrier function, thereby improving the medicaments ability to cross the blood-brain barrier and entering the CNS and thus the spinal cord and/or brain. It is to be noted that it is envisaged that a single nucleic acid sequence may be sufficient for decreasing the blood-brain barrier function; however, it is also within the scope of the invention to combine multiple nucleic acids for decreasing BBB function according to the invention such that an improved decrease of the BBB function can be obtained.

In alternative embodiment, the use of nucleic acid, according to the invention as disclosed above, is provided, for modulating blood-brain barrier function, preferably for increasing or decreasing blood-brain barrier function, preferably in the treatment of stroke, brain trauma, infection, inflammation, multiple sclerosis, HIV infection, Alzheimer's disease, Parkinson's disease, epilepsy, brain tumours, glaucoma, lysosomal storage diseases, prion disease, retinal dysfunction, cerebrovascular disease, migraine or, peroxisome-associated diseases. Preferably, the nucleic acid is a nucleic acid sequence selected from the group consisting of SEQ ID NO 1-152, for increasing blood-brain barrier function.

Furthermore, it is also within the scope of the invention to provide a nucleic acid that encodes a nucleic acid according to the invention, for instance DNA constructs that drive expression of an siRNA duplex or of a nucleic acid (partially) complementary to a nucleic acid sequence selected from SEQ ID No 1-152. Thus, the nucleic acid may also be synthesised de novo, for example by the cell itself.

Different modes or strategies for delivery of the nucleic acid to the brain endothelial cells also fall within the scope of the invention. For instance, in one embodiment, a nucleic acid according to the invention may be coupled to a ligand for delivery into the brain endothelial cells. By coupling a ligand to a nucleic acid according to the invention, the ligand can mediate the uptake of the nucleic acid by the brain endothelial cells, upon which the nucleic acids can execute its function. For instance, a cholesterol conjugate may be used as a ligand and can be used as follows: a nucleic acid is provided, chemically modified and labelled with a cholesterol moiety (Soutschek et al., J. Nature. 2004 Nov. 11; 432(7014):173-8). The nucleic acids can then for instance be injected intravenously, where the cholesterol group enables the siRNAs to be taken up by cells. Alternatively, peptide or nucleotide aptamers may also be used as ligands, and the nucleic acid according to the invention may be coupled thereto (as reviewed e.g. in Cerchia et al. Methods Mol. Biol. 2009; 535:59-78 and Borghouts et al., Comb Chem High Throughput Screen. 2008 February; 11(2):135-45). Aptamers are molecules that are capable of binding to a specific target molecule, for instance a receptor on a cell, resulting in cellular uptake. Aptamers are usually created by selecting them from a large random sequence pool, but natural aptamers also exist in riboswitches. Aptamers are used for both basic research and clinical purposes as macromolecular drugs. These compound molecules have additional research, industrial and clinical applications. Nucleotide aptamers normally contain (usually short) strands of oligonucleotides. Peptide aptamers normally contain a short variable peptide domain, which are often attached at both ends to a protein scaffold. Aptamers can be part of a nucleic acid. (Dassie J P, et al., Nat. Biotechnol. 2009 September; 27(9): 839-49, McNamara J O 2nd, et al., Nat. Biotechnol. 2006 August; 24(8):1005-15). Thus, according to the invention, the nucleic acid may be coupled to a ligand which enables the delivery of the nucleic acid to brain endothelial cells, such that the nucleic acid sequences can have its modulating effect, i.e. increasing or decreasing the blood brain barrier function.

In an alternative embodiment, delivery of a nucleic acid according to the invention may be achieved through a delivery vehicle comprising the nucleic acid. All kinds of delivery vehicle are suitable, as long as the delivery vehicles are capable of introducing the nucleic acid according to the invention in a cell. For instance, a delivery vehicle may be a gene therapy vector. Suitable vectors for instance comprise adenoviral vectors, adeno-associated viral (AAV) vectors, gamma retroviral vectors and lentiviral vectors. Furthermore, a delivery vehicle according to the present invention may also comprise a plasmid delivery system, a virus like particle (VLP), a stable nucleic acid lipid particle (SNALP), a cationic delivery system, a cationic liposomal delivery system, a cationic polymer, a lipoplex, or a liposome. Virus like particles contain viral protein(s) derived from the structural proteins of a virus. In some cases these proteins are embedded within a lipid bilayer. These particles resemble the virus from which they were derived but lack viral nucleic acid, meaning that they are not infectious. Also VLPs are suitable for packaging plasmids or any other nucleic acid, such as for instance pre-miRNAs, pri-miRNAs, shRNAs, miRNA duplexes, siRNA duplexes. By modifications of the viral proteins and linkage of other molecules to the surface of the particle their tropism can be modulated. Cationic macromolecules can also be used for delivery vehicles, the two major classes being lipids and polymers. Examples of cationic vectors are liposomes (lipoplexes) and polyethelyenimine (PEI) (polyplexes).

The invention also includes the use of a nucleic acid according to the invention, the use of a nucleic acid coupled to a ligand according to the invention, or the use of a delivery vehicle according to the invention, for modulating the blood-brain barrier function.

The nucleic acids according to the invention, i.e. for increasing or decreasing the blood-brain barrier function, which may also comprise a nucleic acid coupled to a ligand or a delivery vehicle according to the invention, may be incorporated into a pharmaceutical composition suitable for administration. Such a pharmaceutical composition may comprise a pharmaceutically acceptable carrier, which is intended to include any and all solvents, dispersion media, coatings, isotonic and adsorption delaying agents and the like compatible with pharmaceutical administration. Furthermore, the pharmaceutical composition may also comprise medicaments that are suitable for use in combination with a nucleic acid according to the invention in a treatment for increasing and/or decreasing the blood-brain barrier. Routes of administration of pharmaceutical compositions according to the invention comprise oral administration, application on the skin, or injection, but is not limited thereto.

In another embodiment, a method is provided for modulating the blood brain barrier by providing the nucleic acids as described above. The blood brain barrier can be modulated in vitro or in vivo. When a method involving modulation of the blood brain barrier is in a human and in vivo, such a method does not involve a method for treatment of the human or animal body practised on the human or animal body. When in any of the methods embodiments, the nucleic acid, or delivery vehicle is provided in vitro, the method may comprise providing a vessel or a dish which contains or comprises the nucleic acid, or delivery vehicle. For example, there may be provided the nucleic acid, or delivery vehicle that is freeze dried in a well (e.g. Reinisalo et al., J Control Release. 2006 Jan. 10; 110(2):437-43 and del Pozo-Rodríguez et al., Eur J Pharm Biopharm. 2009 February; 71(2):181-9). In a further embodiment, the nucleic acid or delivery vehicle is introduced in a cell, preferably a brain endothelial cell. Said brain endothelial cell can be a primary cell or a cell line, preferably HCMEC/D3 (Weksler et al., the FASEB Journal. 2005; 19:1872-1874). The current invention now provides for the above methods, and now makes it possible to modulate, e.g. in vitro, the blood-brain barrier by the provision of said nucleic acid, protein or delivery vehicle. These methods may in particular be useful in the study of the blood-brain barrier.

Alternatively, the methods of the invention also provides for the modulation of the blood brain barrier in animal models that would be of particular interest for studying the effect of modulating BBB function. For instance, animal models exist for Alzheimer's and Parkinson's disease, as well multiple sclerosis Studying the effect of the nucleic acids, and/or delivery vehicles according to the invention in these models may be of interest for the development of novel therapies, but is not limited thereto. As long as in an animal model for a disease wherein the blood brain barrier is impaired, it would be of interest to study the effect of increasing or decreasing the blood brain barrier permeability, the nucleic acids and proteins according to the invention may be used.

The invention further also provides for an assay (method) for screening for compounds that may modulate the blood brain barrier function comprising the steps of incubating a cell in the presence of a compound to be tested, and determining the expression level of a nucleic acid sequence selected from the group of SEQ ID No. 1-152, wherein the expression level of said nucleic acid sequence is compared with the expression level of said nucleic acid sequence determined in a cell incubated without the presence of said compound to be tested.

Cells may for instance be contained in multi-well plates either in suspension or attached. The cells may be incubated in the presence of a compound, for instance by adding the compound to the cell culturing medium. Cell culturing medium is defined as a solution which provides the cell with nutrients such that the cells may be sustained. Alternatively, the compound may also be provided in a suitable standard buffer, such as for instance phosphate buffered saline (PBS), for a period of time such that the cells are contacted with the compound. Any method incubating the cells with the compounds are allowed, as long as the compound may have its effect on the cells. When the cells have been incubated with the said compound, the nucleic acid sequence expression level is determined. The nucleic acid sequences from the group of SEQ ID No. 1-152 are suitable in a screening assay for compounds that modulate the BBB. The term modulation means either increasing or decreasing. When the expression level of a said nucleic acid sequence is upregulated in a cell incubated in the presence of a compound as compared to a cell incubated in the absence of said compound, such a compound is capable of increasing the BBB function, and when the expression level of a said nucleic acid sequence is downregulated in the presence of a compound as compared to a cell incubated without the presence of said compound to be tested, such a compound is capable of decreasing the BBB function. In general, compounds that result in either an up- or down-regulation of a nucleic acid sequence selected from the group of SEQ ID No. 1-152 of at least 2-fold may be considered as compounds that are identified to have the potential to modulate the BBB. In general, the higher the up- or downregulation, the lowest number of potential compounds may be identified but these compounds also may have a stronger effect on BBB modulation. Not only single compounds may be tested, but it is also envisaged that combinations of compounds may be tested for their potential effect on modulation of the BBB function. Furthermore, it is also within the scope of the invention to determine, in an assay for screening for compounds that modulate the BBB function, the expression levels of more than one nucleic acid sequence selected from the group consisting of SEQ ID No. 1-152.

In a different embodiment, the assay as disclosed above comprises in the step of incubating a cell in the presence of a compound to be tested, astrocyte conditioned medium in addition and/or wherein the assay further comprises the step of: incubating the cell in the presence of astrocyte conditioned medium, before and/or after the step of incubating a cell in the presence of a compound to be tested. Astrocyte conditioned medium (ACM) is defined as cell-free medium in which primary human astrocytes have been cultured (see Example 1). The astrocyte conditioned medium, which may preferably be fetal astrocyte medium, has an effect on the level of expression of SEQ ID No 1-152, i.e. the level of expression is increased, and thus the BBB function is increased. Therefore, ACM increases the expression of a nucleic acid sequence selected from the group of SEQ ID No. 1-152, and the said medium thus has an effect on the expression said nucleic acid sequences. Accordingly, compounds may interact with the ACM, or influence the interaction between ACM and the endothelial brain cells. Thus, when compounds interact with ACM or influence the interaction between ACM and the endothelial brain cells, the effect of ACM with regard to increasing the expression of a nucleic acid from SEQ ID No. 1-152 may be modulated. Thus, the expression of a nucleic acid sequence selected from the group of SEQ ID No. 1-152 may be further increased, or is decreased (or even completely blocked), in a cell incubated in the presence of astrocyte conditioned medium and a compound, as compared to a cell incubated in the presence of ACM and the absence of the said compound. For example, compounds may have an effect on the expression of a nucleic acid from SEQ ID No. 1-152 induced by the astrocyte conditioned medium, for instance compounds may interfere, inhibit, enhance pathways/receptors and the like involved in the regulation of the expression of a nucleic acid sequence from the group of SEQ ID No. 1-152 by the astrocyte conditioned medium and thereby increase or decrease the effect of the ACM on the expression level of a nucleic acid sequence from SEQ ID No. 1-152. Such an increasing or decreasing effect may not be observed as effectively without the step of incubating the cell in the presence of astrocyte conditioned medium, although it is to be understood that the use of the astrocyte medium is optional. According to this embodiment, when the expression level of said nucleic acid sequence is upregulated in a cell incubated in the presence of a compound and in the presence of ACM (which may be present before, during and/or after the incubation in the presence of said compound) as compared to a cell incubated without the presence of a compound, such a compound is capable of increasing the BBB function. When the expression level of said nucleic acid sequence is downregulated in a cell incubated in the presence of a compound and in the presence of ACM (which may be present before, during and/or after the incubation in the presence of said compound) as compared to a cell incubated without the presence of a compound, such a compound is capable of decreasing the BBB function. In general, compounds that result in either an up- or downregulation of (a) nucleic acid(s) sequence(s) selected from the group of SEQ ID No. 1-152 of at least 2-fold may be considered as compounds that are identified to have the potential to modulate the BBB function, i.e. increase or decrease the BBB function It is preferred to use brain endothelial cells in the above assays, as the BBB largely comprises brain endothelial cells, and thus, these cells are preferred. Therefore, in a further embodiment, the cell in the assays as described, is a brain endothelial cell. The brain endothelial cell can be a primary cell, but a cell line is preferred. Human primary brain endothelial cells may be obtained from subjects from biopsy material, and thus supply might be limited and restricted by regulations as consent is required, furthermore, primary cells have a limited life span. Therefore, it is preferred to use an immortalized human brain endothelial cell line, such as for instance HCMEC/D3.

In the above assays, the expression level of a nucleic acid sequence from SEQ ID No 1-152 is determined. However, it is to be noted that it is also possible to determine the expression level of several nucleic acid sequences from SEQ ID No 1-152, for example simultaneously. In one embodiment, the expression level of the nucleic acid sequences in the above assays can be determined with a microarray (Li and Ruan, Anal Bioanal Chem. 2009 June; 394(4):1117-24). A microarray is a multiplex technology used in molecular biology and in medicine which consists of an arrayed series of thousands of microscopic spots of oligonucleotides, each containing picomoles of a specific oligonucleotide sequence. This sequence is complementary to a sequence from SEQ ID No 1-152 that are used as probes to hybridize to a target nucleic acid sequence under suitable, preferably high-stringency conditions. The target nucleic acid sequences can be labelled for example with a fluorescent label, and probe-target hybridization can thus be detected and quantified by measuring the fluorescence intensity. For instance, in example 2 it is described in close detail how a microarray may be performed. In an alternative embodiment, the expression level is determined with a PCR reaction, preferably a quantitative PCR reaction. In example 4 it is described in close detail how such a PCR can be performed; in addition and based on the sequences disclosed herein any skilled person understands how to perform such PCR, preferably quantitative PCR reaction (as described in detail in Mestdagh et al., Nucleic Acids Res. 2008 December; 36(21) and Chen et al., Nucleic Acids Res. 2005 Nov. 27; 33(20)).

In another embodiment, the expression level of a nucleic acid sequence selected from the group consisting of SEQ ID No 1-152 may be determined with the use of a reporter construct. A reporter gene construct expresses a reporter gene, for instance Green Fluorescent Protein (GFP) or luciferase. The reporter gene construct thus expresses a mRNA transcript that encodes GFP. Within the 3' untranslated region of the GFP transcript, a complementary target sequence, or multiple complementary target sequences can be introduced, such that a nucleic acid sequence from the group consisting of SEQ D No. 1-152 can bind to the complementary target sequence (Brown B D, et al. Nat. Med. 2006 May; 12(5):585-91). The reporter gene construct can be introduced in a cell transiently, for instance via transfection, or may be stably introduced, for instance via recombination or transduction. As the nucleic acid sequence from the group consisting of SEQ ID No. 1-152 targets the reporter gene construct via complementary base paring and/or RNA interference, the level of expression of the reporter gene is controlled by level of expression of the said nucleic acid sequence, because binding and/or cleavage of the nucleic acid sequence to the reporter transcript reduces mRNA translation into protein. Thus, in case a GFP construct with a complementary target sequence, or multiple target sequences to a sequence selected from the group consisting of SEQ. ID. No. 1-152 is used in the said assay, the GFP expression level is inversely proportional to the level of expression of a nucleic acid comprising a nucleic acid sequence selected from the group consisting of SEQ ID No. 1-152. Thus, a reduction in the GFP expression corresponds to an increase in the said nucleic acid sequence expression and thus an increase in the BBB function, while an increase in GFP expression corresponds to a decrease in the said nucleic acid sequence expression and thus a decrease in the BBB function. In a further embodiment, in an assay for screening for compounds that modulate the blood brain barrier function as disclosed above, the expression level of a nucleic acid sequence selected from the group of SEQ ID No. 1-152 is determined with a microarray, a PCR reaction, a quantitative PCR or a reporter gene construct.

EXAMPLES

Example 1

Astrocyte Factors Increase the Blood Brain Barrier Function

The effect of soluble astrocyte factors on the blood brain barrier function was evaluated in vitro with brain endothelial cells. For this, 200.000 HCMEC/D3 cells, a brain endothelial cell line, were seeded at confluency onto each well of an 8W10+ ECIS array coated with collagen cells. Cells were incubated in in EGM-2 medium (Clonetics) containing 2.5% foetal calf serum, or in a 1:1 mixture of astrocyte conditioned medium (cell free medium from human astrocytes cultured for 7 days in standard DMEM (Gibco) medium) and EGM-2 medium containing 2.5% foetal calf serum. The ECIS™ Model 1600R (Applied BioPhysics, Troy, N.Y., USA) was used to measure the transendothelial electrical resistance (TEER) for 60-80 hours using ECIS according to the manufacturer's instructions and impedance was measured at 6000 Hz in real time. The result of the TEER measurements is shown in FIG. 1. After about 70 hours post-seeding, the TEER values of a control well, in which the endothelial brain cells were incubated without astrocyte conditioned medium (ACM) was about 1250 ohm. The cells incubated with ACM had a value of about 1700 ohm. Thus, the endothelial brain cells incubated in ACM had an increased TEER value, representing an increased BBB function. It is concluded that ACM improves BBB function.

Example 2

Astrocyte Conditioned Medium Regulates miRNA Expression miRNAs were studied for their involvement in the blood-brain barrier function. Large-scale expression analysis was performed of miRNAs in HCMEC/D3s either or not treated with astrocyte conditioned medium. 13-18 µg total RNA was isolated using Trizol from $1\times10^6$ brain endothelial cells which were cultured in 50% astrocytes-conditioned medium/50% complete EGM2 for 48 h. Before mRNA and miRNA profiling the RNA samples underwent quality control by Agilent Bioanalyzer Picochip analysis (RIN>9). mRNA was analysed at ServiceXS (Leiden, The Netherlands). In brief, mRNA was amplified and biotinylated using the Illumina TotalPrep RNA amplification Kit (Ambion, Austin, Tex.), and randomly allocated to Sentrix HT12 Expression bead chip arrays (Illumina, San Diego, Calif.), interrogating 48,000 individual probes representing 24,600 well annotated genes from the human genome. cRNA samples were hybridized to the bead-chip arrays, followed by scanning and feature extraction. Array data were extracted and normalized average bead summary data were generated using Illumina BeadStudio software. Bead summary intensities for individual probes were normalized using inter-array Quantile normalization using R/Bioconductor (www.bioconductor.org). Differential expression in ACM-treated versus control cells was assessed by a Baysian statistics t-test (Cyber-T) (Baldi and Long 2001) and adjusted for multiple testing by using Benjamini and Hochberg's method (Benjamini and Hochberg 1995). Differential genes were considered significant if the P values were <0.05, thereby controlling the False Discovery Rate to be <5%.

For miRNA expression analyses (Exiqon, Denmark), 1 μg total RNA from sample and reference was labeled with Hy3™ and Hy5™ fluorescent label, respectively, using the miRCURY™ LNA Array power labeling kit (Exiqon, Denmark) following the procedure described by the manufacturer. The Hy3™-labeled samples and a Hy5™-labeled reference RNA sample were mixed pair-wise and hybridized to the miRCURY™ LNA array version 11.0 (Exiqon, Denmark), which contains capture probes targeting all miRNAs for human, mouse or rat registered in the miRBASE version 12.0 at the Sanger Institute (Sanger Institute details: http://www.mirbase.org/). The hybridization was performed according to the miRCURY™ LNA array manual using a Tecan HS4800 hybridization station (Tecan, Austria). After hybridization the microarray slides were scanned and stored in an ozone free environment (ozone level below 2.0 ppb) in order to prevent potential bleaching of the fluorescent dyes. The miRCURY™ LNA array microarray slides were scanned using the Agilent G2565BA Microarray Scanner System (Agilent Technologies, Inc., USA) and the image analysis was carried out using the ImaGene 8.0 software (BioDiscovery, Inc., USA). Generation and statistical analysis of miRNA expression profiles were performed similarly using R/Bioconductor. Quantile normalization of intensities of individual spots was followed by reference colour adjustment and ratios of probes representing the same miRNA were averaged. Differential expression of ACM-treated versus control samples was determined by Baysian statistics t-test (Baldi and Long 2001) and multiple testing adjustment using Benjamini and Hochberg's method (Benjamini and Hochberg 1995).

Analyses of array hybridizations revealed the putative miRNA expression of in HCMEC/D3s and confirmed the expression of various miRNAs previously described to be expressed in endothelial cells (Kuehbacher et al. 2007; Poliseno et al. 2006; Suarez et al. 2007; Tuccoli et al. 2006; Wurdinger et al. 2008). Exposure of HCMEC/D3s to astrocyte conditioned medium changed the expression level of miRNAs (Table I; SEQ ID No. 1-152) at least 2-fold as compared to HCMEC/D3s not exposed to astrocyte conditioned medium. The top 4 of the most notable changes were observed for miR-519d, miR-668, miR-888* and miR-886-5p, which were upregulated by 5-, 6-, 6-, and 7-fold respectively. It was concluded that an increase of the nucleic acid sequences of SEQ ID No. 1-152 increases the BBB function. Furthermore, it was also concluded that these (putative) miRNA sequences can be used as markers for BBB function, and thus are suitable for use in assays in which compounds are screened for that modulate, i.e. increase or decrease, the BBB function. Finally, it was also concluded that these nucleic acid sequences, or nucleic acids comprising nucleic acid sequences with some degree of identity therewith, are suitable for increasing the BBB function, and that nucleic acids with some degree of complementarity with the nucleic acid sequences from SEQ ID No. 1-152 would be suitable for downregulating the BBB function.

Example 3

Figure 2:
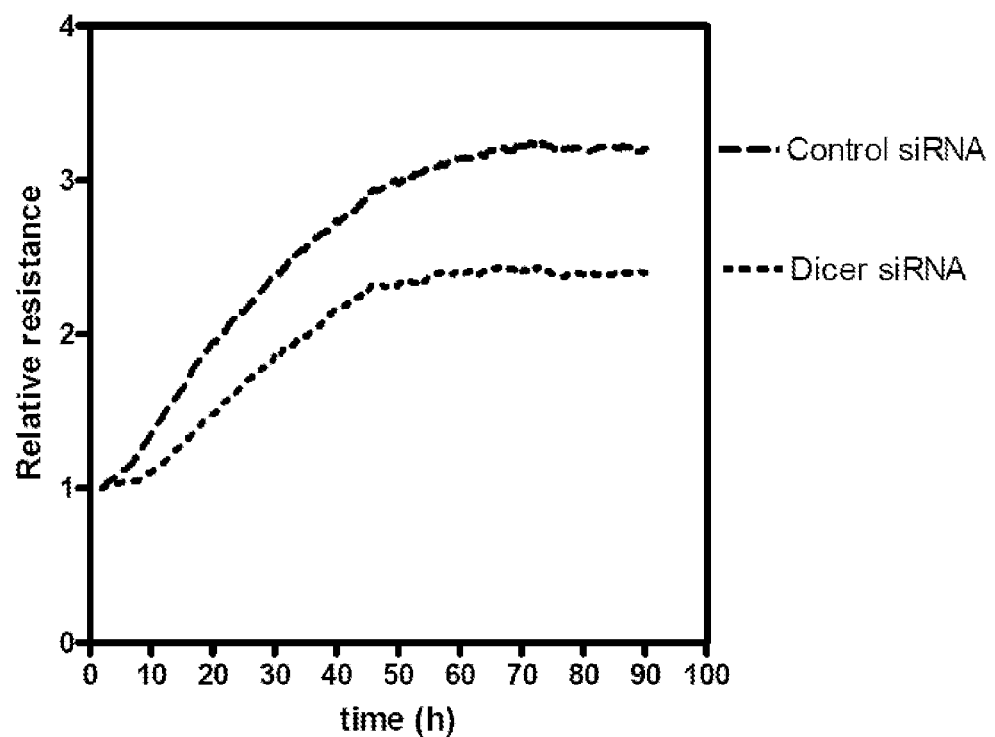
FIG. 2 is a graph of the relative resistance (in terms of TEER) of endothelial brains cells transfected with an siRNA against DICER or a silencing control siRNA at 48 hours post-transfection relative to 0 hours (where the relative resistance is set at 1).

Blocking the RNAi Pathway Via Knock-down of DICER Results in a Decrease in BBB Function To confirm that the nucleic acids according to the invention, in particular miRNAs having a sequence according to any of seq ID no 1-152 improve BBB function, the effect of Dicer knock-down with an siRNA against Dicer was studied. Knocking down Dicer should result in blocking the processing of pri-miRNAs and hence prevent incorporation of endogenous miRNAs into the RISC complex. Endothelial brain cells were transfected with an siRNA against DICER (sc-40489, Santa Cruz) or a silencing control siRNA (also obtained from Santa Cruz) and transfections were performed with DharmaFECT-4 according to the manufacturer's instructions (Dharmacon). 48 hours post-transfection, the cells were seeded in an 8W10+ECIS array as described above and TEER was measure as described above. The relative resistance measured is plotted in FIG. 2. The relative resistance at 0 hours was set at 1. As can be witnessed from said figure, knocking down the DICER enzyme reduced the resistance of the in endothelial brain cells, confirming that indeed the RNA interference pathway and/or miRNA biogenesis pathway is involved and required for BBB function. These data therefore confirm the concept that the nucleic acid sequences from SEQ ID No. 1-152 are involved in regulating the BBB function, in particular in increasing the BBB function.

Example 4

Figure 3:
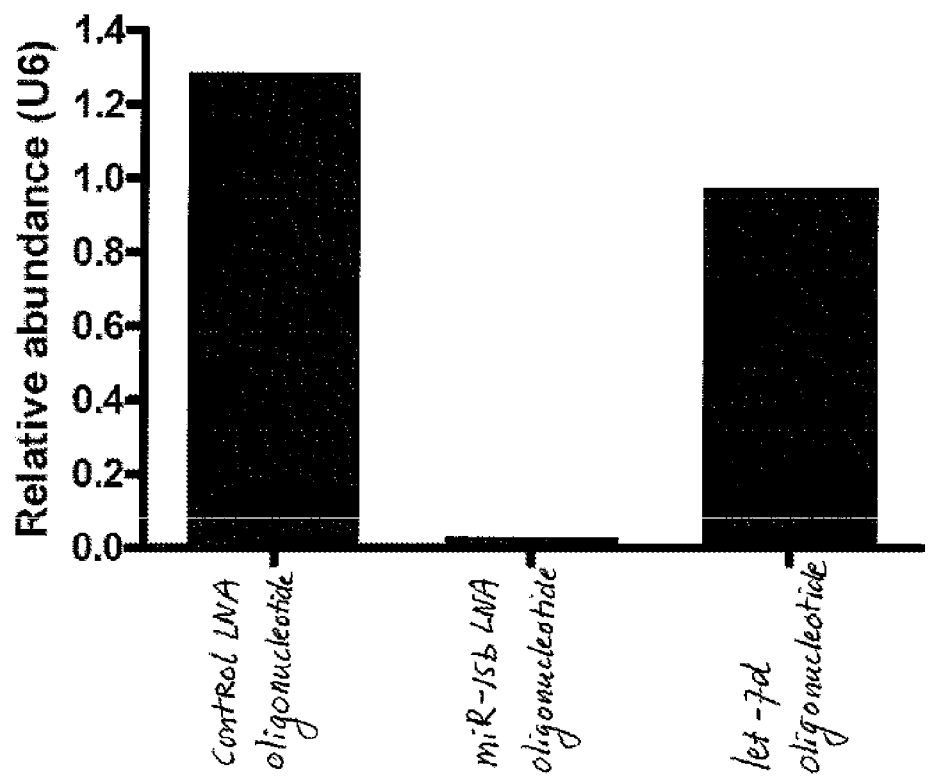
FIG. 3 is a graph of the relative abundance of expression of endogenous miR-15b in HCMEC/D3 cells transfected with miR-15b LNA, let-7d, and control LNA oligonucleotides.

Blocking miR-15b Decreases BBB Function miRNA blocking was carried out using miRNA specific (miR-15b, let-7d) (miR-15b, TGTAAACCATGATGTGCT-GCTA SEQ ID NO:154; let-7d, AACTATGCAACCTAC-TACCCT SEQ ID NO:155) and scrambled control (mir-CURY knockdown probe: code 199002-04) fluorescein-labelled LNA oligonucleotides (Exiqon, Vedbaek, Denmark), transfected into HCMEC/D3 in 100.00 cells per 8W10 ECIS array well, at a final concentration of 40 nM in a final volume of 250 μl by DharmaFECT-4 reagent (Dharmacon). Transfection efficiency ranged between 80 and 90%, determined by microscopic fluorescein detection. The level of expression of the endogenous miR-15b was subsequently determined by PCR, using the miRCURYTM LNA microRNA PCR system (Exiqon). In the control (scrambled), miR-15b and let7 LNA oligonucleotides transfections, relative abundance of a miRNA-15b was determined and defined as (Ct (sample)-Ct (U6snRNA)$^2$). Transfection of a miR-15b specific LNA oligonucleotide resulted in a potent reduction of miR-15b as detected with the PCR assay (FIG. 3) after 48 hours. Next, endothelial brain cells were transfected either with the miR-15b LNA oligonucleotide or the scrambled control at a final concentration of 40 nM by DharmaFECT-4 reagent (Dharmacon). 48 hours post-transfection, the cells were seeded in an 8W10+ECIS array as described above and TEER was measure as described above. The relative resistance that was now measured is plotted in FIG. 4. The relative resistance at 0 hours was set at 1. The results of real-time TEER analysis show that blocking a miRNA selected from the group consisting of SEQ ID No. 1-152, in particular miR-15b reduced the resistance barrier properties. Thus, blocking miR-15b decreases the BBB function. Thus, this experiment confirms that nucleic acids with some degree of complementarity with the nucleic acid sequences from SEQ ID No. 1-152 are suitable for downregulating the BBB function.

Example 5

Lentiviral Delivery of and microRNAs

Figure 6:
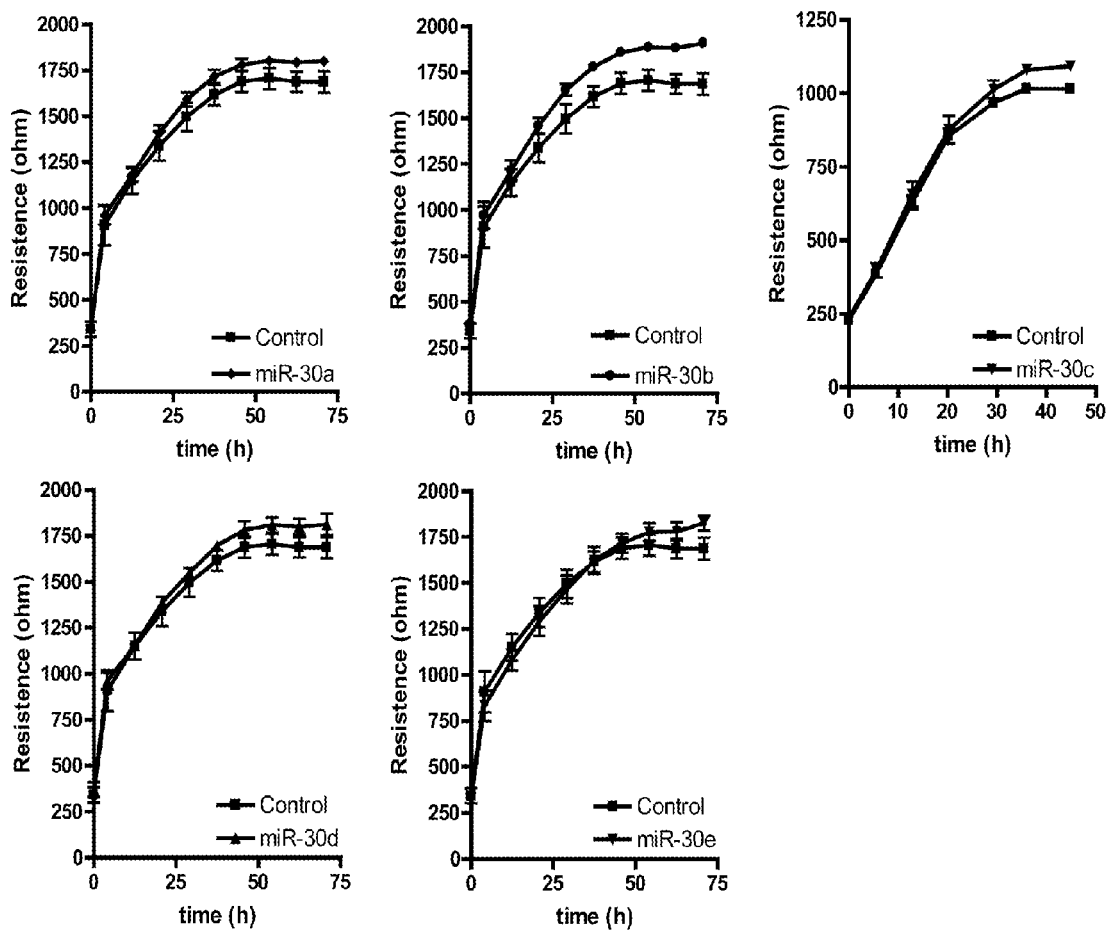
FIG. 6 shows graphs of TEER measurements over time in human brain endothelial cells transduced with lentiviruses containing microRNA miR-30a, miR-30b, miR-30c, miR-30d, or miR-30e.

MiRNAs were cloned from human genomic DNA and ligated between the SmaI and EcoRI restriction sites of pRRL-cPPT-CMV-X2-PRE-SIN-IRES-eGFP vector (kindly provided by Dr. J. Seppen, Department of Experimental Hepatology, Academic Medical Center, Amsterdam, The Netherlands). Recombinant lentiviruses were produced by co-transfecting subconfluent HEK 293T cells with the specific expression plasmids and packaging plasmids (pMDLg/pRRE, pRSV-Rev and pMD2G) using calcium phosphate as a transfection reagent. HEK 293T cells were cultured in DMEM supplemented with 10% FCS, 1% penicillin/streptomycin, in a 37° C. incubator with 5% CO2. Infectious lentiviruses were collected 48 h after transfection. The supernatant was centrifuged to remove cell debris and stored at −80° C. For barrier resistance analyses hCMEC/D3 human brain endothelial cells were transduced with the lentiviruses containing the microRNAs. The ECIS™ Model 1600R (Applied BioPhysics, Troy, N.Y., USA) was used to measure the transendothelial electrical resistance (TEER) for 60-80 hours using ECIS according to the manufacturer's instructions and impedance was measured at 6000 Hz in real time. The result of the TEER measurements is shown in FIG. 6. The results of real-time TEER analysis show that increasing the amount of an microRNA selected from the group consisting of SEQ ID No. 1-152, in particular miR-30a, miR-30b, miR-30c, miR-30d, miR-30e enhanced the resistance barrier properties. Thus, increasing miR-30a, miR-30b, miR-30c, miR-30d, miR-30e increases the BBB function. Thus, this experiment confirms that nucleic acids from SEQ ID No. 1-152 are suitable for increasing the BBB function.

TABLE 1

| SEQ ID | miRNA | Fold induction | RNA sequence |
| --- | --- | --- | --- |
| SEQ ID No. 1 | miR-886-5p | 7.13 | CGGGUCGGAGUUAGCUCAAGCGG |
| SEQ ID No. 2 | miR-888* | 6.00 | GACUGACACCUCUUUGGGUGAA |
| SEQ ID No. 3 | miR-668 | 5.86 | UGUCACUCGGCUCGGCCCACUAC |
| SEQ ID No. 4 | miR-519d | 5.07 | CAAAGUGCCUCCCUUUAGAGUG |
| SEQ ID No. 5 | miR-487b | 4.88 | AAUCGUACAGGGUCAUCCACUU |
| SEQ ID No. 6 | miR-494 | 4.85 | UGAAACAUACACGGGAAACCUC |
| SEQ ID No. 7 | miR-106b | 4.74 | UAAAGUGCUGACAGUGCAGAU |
| SEQ ID No. 8 | miR-1259 | 4.68 | AUAUAUGAUGACUUAGCUUUU |
| SEQ ID No. 9 | miR-100 | 4.49 | AACCCGUAGAUCCGAACUUGUG |
| SEQ ID No. 10 | miR-27a | 4.37 | UUCACAGUGGCUAAGUUCCGC |
| SEQ ID No. 11 | miR-31 | 4.33 | AGGCAAGAUGCUGGCAUAGCU |
| SEQ ID No. 12 | miR-889 | 4.29 | UUAAUAUCGGACAACCAUUGU |
| SEQ ID No. 13 | miR-26a | 4.23 | UUCAAGUAAUCCAGGAUAGGCU |
| SEQ ID No. 14 | miR-15a | 4.23 | UAGCAGCACAUAAUGGUUUGUG |
| SEQ ID No. 15 | miR-126* | 4.22 | CAUUAUUACUUUUGGUACGCG |
| SEQ ID No. 16 | miR-195 | 4.19 | UAGCAGCACAGAAAUAUUGGC |
| SEQ ID No. 17 | miR-24-1* | 4.15 | UGCCUACUGAGCUGAUAUCAGU |
| SEQ ID No. 18 | miR-15b | 4.05 | UAGCAGCACAUCAUGGUUUACA |
| SEQ ID No. 19 | miR-193a-3p | 4.03 | AACUGGCCUACAAAGUCCCAGU |
| SEQ ID No. 20 | miR-551b | 3.99 | GCGACCCAUACUUGGUUUCAG |
| SEQ ID No. 21 | miR-202 | 3.99 | AGAGGUAUAGGGCAUGGGAA |
| SEQ ID No. 22 | miR-1274b | 3.94 | UCCCUGUUCGGGCGCCA |
| SEQ ID No. 23 | miR-1275 | 3.91 | GUGGGGGAGAGGCUGUC |
| SEQ ID No. 24 | miR-19a | 3.86 | UGUGCAAAUCUAUGCAAAACUGA |
| SEQ ID No. 25 | let-7g | 3.84 | UGAGGUAGUAGUUUGUACAGUU |

TABLE 1-continued

| SEQ ID | miRNA | Fold induction | RNA sequence |
|---|---|---|---|
| SEQ ID No. 26 | miR-18b | 3.82 | UAAGGUGCAUCUAGUGCAGUUAG |
| SEQ ID No. 27 | miR-29c | 3.82 | UAGCACCAUUUGAAAUCGGUUA |
| SEQ ID No. 28 | miR-874 | 3.81 | CUGCCCUGGCCCGAGGGACCGA |
| SEQ ID No. 29 | miR-1274a | 3.80 | GUCCCUGUUCAGGCGCCA |
| SEQ ID No. 30 | miR-1908 | 3.77 | CGGCGGGGACGGCGAUUGGUC |
| SEQ ID No. 31 | miR-887 | 3.70 | GUGAACGGGCGCCAUCCCGAGG |
| SEQ ID No. 32 | miR-30b | 3.70 | UGUAAACAUCCUACACUCAGCU |
| SEQ ID No. 33 | miR-106a | 3.66 | AAAAGUGCUUACAGUGCAGGUAG |
| SEQ ID No. 34 | miR-584 | 3.66 | UUAUGGUUUGCCUGGGACUGAG |
| SEQ ID No. 35 | let-7b | 3.65 | UGAGGUAGUAGGUUGUGUGGUU |
| SEQ ID No. 36 | miR-1260 | 3.64 | AUCCCACCUCUGCCACCA |
| SEQ ID No. 37 | miR-30c | 3.63 | UGUAAACAUCCUACACUCUCAGC |
| SEQ ID No. 38 | miR-30e | 3.61 | UGUAAACAUCCUUGACUGGAAG |
| SEQ ID No. 39 | let-7e | 3.58 | UGAGGUAGGAGGUUGUAUAGUU |
| SEQ ID No. 40 | miR-19b | 3.57 | UGUGCAAAUCCAUGCAAAACUGA |
| SEQ ID No. 41 | miR-221 | 3.55 | AGCUACAUUGUCUGCUGGGUUUC |
| SEQ ID No. 42 | miR-25* | 3.54 | AGGCGGAGACUUGGGCAAUUG |
| SEQ ID No. 43 | miR-26b | 3.53 | UUCAAGUAAUUCAGGAUAGGU |
| SEQ ID No. 44 | miR-423-5p | 3.52 | UGAGGGGCAGAGAGCGAGACUUU |
| SEQ ID No. 45 | miR-18a | 3.49 | UAAGGUGCAUCUAGUGCAGAUAG |
| SEQ ID No. 46 | let-7d | 3.47 | AGAGGUAGUAGGUUGCAUAGUU |
| SEQ ID No. 47 | let-7c | 3.43 | UGAGGUAGUAGGUUGUAUGGUU |
| SEQ ID No. 48 | miR-17 | 3.42 | CAAAGUGCUUACAGUGCAGGUAG |
| SEQ ID No. 49 | miR-1284 | 3.41 | UCUAUACAGACCCUGGCUUUUC |
| SEQ ID No. 50 | miR-424 | 3.41 | CAGCAGCAAUUCAUGUUUUGAA |
| SEQ ID No. 51 | miR-374a | 3.39 | UUAUAAUACAACCUGAUAAGUG |
| SEQ ID No. 52 | miR-29b | 3.36 | UAGCACCAUUUGAAAUCAGUGUU |
| SEQ ID No. 53 | miR-30d | 3.35 | UGUAAACAUCCCCGACUGGAAG |
| SEQ ID No. 54 | miR-634 | 3.35 | AACCAGCACCCCAACUUUGGAC |
| SEQ ID No. 55 | miR-1285 | 3.34 | UCUGGGCAACAAAGUGAGACCU |
| SEQ ID No. 56 | miR-1308 | 3.31 | GCAUGGGUGGUUCAGUGG |
| SEQ ID No. 57 | miR-138-1* | 3.31 | GCUACUUCACAACACCAGGGCC |
| SEQ ID No. 58 | miR-381 | 3.30 | UAUACAAGGGCAAGCUCUCUGU |
| SEQ ID No. 59 | miR-222 | 3.27 | AGCUACAUCUGGCUACUGGGU |
| SEQ ID No. 60 | miR-27b | 3.23 | UUCACAGUGGCUAAGUUCUGC |
| SEQ ID No. 61 | miR-20b | 3.22 | CAAAGUGCUCAUAGUGCAGGUAG |
| SEQ ID No. 62 | miR-130a | 3.21 | CAGUGCAAUGUUAAAAGGGCAU |
| SEQ ID No. 63 | miR-129* | 3.18 | AAGCCCUUACCCCAAAAAGUAU |
| SEQ ID No. 64 | miR-103 | 3.13 | AGCAGCAUUGUACAGGGCUAUGA |

TABLE 1-continued

| SEQ ID | miRNA | Fold induction | RNA sequence |
|---|---|---|---|
| SEQ ID No. 65 | miR-301a | 3.11 | CAGUGCAAUAGUAUUGUCAAAGC |
| SEQ ID No. 66 | miR-766 | 3.11 | ACUCCAGCCCCACAGCCUCAGC |
| SEQ ID No. 67 | miR-101 | 3.10 | UACAGUACUGUGAUAACUGAA |
| SEQ ID No. 68 | miR-933 | 3.08 | UGUGCGCAGGGAGACCUCUCCC |
| SEQ ID No. 69 | miR-107 | 3.06 | AGCAGCAUUGUACAGGGCUAUCA |
| SEQ ID No. 70 | miR-33a | 3.05 | GUGCAUUGUAGUUGCAUUGCA |
| SEQ ID No. 71 | miR-105 | 3.04 | UCAAAUGCUCAGACUCCUGUGGU |
| SEQ ID No. 72 | miR-20a | 3.04 | UAAAGUGCUUAUAGUGCAGGUAG |
| SEQ ID No. 73 | miR-151-5p | 3.02 | UCGAGGAGCUCACAGUCUAGU |
| SEQ ID No. 74 | miR-320a | 3.00 | AAAAGCUGGGUUGAGAGGGCGA |
| SEQ ID No. 75 | miR-31* | 2.99 | UGCUAUGCCAACAUAUUGCCAU |
| SEQ ID No. 76 | miR-665 | 2.98 | ACCAGGAGGCUGAGGCCCCU |
| SEQ ID No. 77 | let-7a | 2.97 | UGAGGUAGUAGGUUGUAUAGUU |
| SEQ ID No. 78 | miR-149* | 2.97 | AGGGAGGGACGGGGGCUGUGC |
| SEQ ID No. 79 | miR-519e* | 2.90 | UUCUCCAAAAGGGAGCACUUUC |
| SEQ ID No. 80 | miR-30a | 2.90 | UGUAAACAUCCUCGACUGGAAG |
| SEQ ID No. 81 | miR-93 | 2.89 | CAAAGUGCUGUUCGUGCAGGUAG |
| SEQ ID No. 82 | miR-32 | 2.88 | UAUUGCACAUUACUAAGUUGCA |
| SEQ ID No. 83 | miR-1827 | 2.87 | UGAGGCAGUAGAUUGAAU |
| SEQ ID No. 84 | miR-184 | 2.86 | UGGACGGAGAACUGAUAAGGGU |
| SEQ ID No. 85 | miR-23a | 2.86 | AUCACAUUGCCAGGGAUUUCC |
| SEQ ID No. 86 | miR-1184 | 2.83 | CCUGCAGCGACUUGAUGGCUUCC |
| SEQ ID No. 87 | miR-454 | 2.83 | UAGUGCAAUAUUGCUUAUAGGGU |
| SEQ ID No. 88 | miR-130b | 2.82 | CAGUGCAAUGAUGAAAGGGCAU |
| SEQ ID No. 89 | miR-1265 | 2.79 | CAGGAUGUGGUCAAGUGUUGUU |
| SEQ ID No. 90 | miR-1201 | 2.78 | AGCCUGAUUAAACACAUGCUCUGA |
| SEQ ID No. 91 | miR-99b | 2.74 | CACCCGUAGAACCGACCUUGCG |
| SEQ ID No. 92 | miR-513a-5p | 2.70 | UUCACAGGGAGGUGUCAU |
| SEQ ID No. 93 | miR-185 | 2.68 | UGGAGAGAAAGGCAGUUCCUGA |
| SEQ ID No. 94 | miR-24 | 2.67 | UGGCUCAGUUCAGCAGGAACAG |
| SEQ ID No. 95 | miR-191 | 2.65 | CAACGGAAUCCCAAAAGCAGCUG |
| SEQ ID No. 96 | miR-29a | 2.65 | UAGCACCAUCUGAAAUCGGUUA |
| SEQ ID No. 97 | miR-22 | 2.63 | AAGCUGCCAGUUGAAGAACUGU |
| SEQ ID No. 98 | miR-34a | 2.61 | UGGCAGUGUCUUAGCUGGUUGU |
| SEQ ID No. 99 | miR-491-3p | 2.59 | CUUAUGCAAGAUUCCCUUCUAC |
| SEQ ID No. 100 | miR-140-3p | 2.59 | UACCACAGGGUAGAACCACGG |
| SEQ ID No. 101 | miR-628-3p | 2.59 | UCUAGUAAGAGUGGCAGUCGA |
| SEQ ID No. 102 | miR-340 | 2.58 | UUAUAAAGCAAUGAGACUGAUU |

TABLE 1-continued

| SEQ ID | miRNA | Fold induction | RNA sequence |
|---|---|---|---|
| SEQ ID No. 103 | miR-34b | 2.57 | CAAUCACUAACUCCACUGCCAU |
| SEQ ID No. 104 | miR-25 | 2.56 | CAUUGCACUUGUCUCGGUCUGA |
| SEQ ID No. 105 | miR-181a | 2.56 | AACAUUCAACGCUGUCGGUGAGU |
| SEQ ID No. 106 | miR-320b | 2.56 | AAAAGCUGGGUUGAGAGGGCAA |
| SEQ ID No. 107 | miR-320d | 2.53 | AAAAGCUGGGUUGAGAGGA |
| SEQ ID No. 108 | miR-1255a | 2.52 | AGGAUGAGCAAAGAAAGUAGAUU |
| SEQ ID No. 109 | miR-183* | 2.51 | GUGAAUUACCGAAGGGCCAUAA |
| SEQ ID No. 110 | miR-664 | 2.51 | UAUUCAUUUAUCCCCAGCCUACA |
| SEQ ID No. 111 | miR-32* | 2.50 | CAAUUUAGUGUGUGUGAUAUUU |
| SEQ ID No. 112 | miR-574-3p | 2.49 | CACGCUCAUGCACACACCCACA |
| SEQ ID No. 113 | miR-525-5p | 2.48 | CUCCAGAGGGAUGCACUUUCU |
| SEQ ID No. 114 | miR-423-3p | 2.47 | AGCUCGGUCUGAGGCCCCUCAGU |
| SEQ ID No. 115 | miR-519e | 2.45 | AAGUGCCUCCUUUUAGAGUGUU |
| SEQ ID No. 116 | miR-23b | 2.44 | AUCACAUUGCCAGGGAUUACC |
| SEQ ID No. 117 | miR-30e* | 2.44 | CUUUCAGUCGGAUGUUUACAGC |
| SEQ ID No. 118 | miR-549 | 2.43 | UGACAACUAUGGAUGAGCUCU |
| SEQ ID No. 119 | miR-886-3p | 2.42 | CGCGGGUGCUUACUGACCCUU |
| SEQ ID No. 120 | miR-339-5p | 2.41 | UCCCUGUCCUCCAGGAGCUCACG |
| SEQ ID No. 121 | miR-331-3p | 2.39 | GCCCCUGGGCCUAUCCUAGAA |
| SEQ ID No. 122 | miR-589 | 2.38 | UGAGAACCACGUCUGCUCUGAG |
| SEQ ID No. 123 | miR-765 | 2.37 | UGGAGGAGAAGGAAGGUGAUG |
| SEQ ID No. 124 | miR-663 | 2.36 | AGGCGGGGCGCCGCGGGACCGC |
| SEQ ID No. 125 | miR-155 | 2.34 | UUAAUGCUAAUCGUGAUAGGGGU |
| SEQ ID No. 126 | miR-1264 | 2.33 | CAAGUCUUAUUUGAGCACCUGUU |
| SEQ ID No. 127 | miR-320c | 2.32 | AAAAGCUGGGUUGAGAGGGU |
| SEQ ID No. 128 | miR-1290 | 2.32 | UGGAUUUUUGGAUCAGGGA |
| SEQ ID No. 129 | miR-374b | 2.30 | AUAUAAUACAACCUGCUAAGUG |
| SEQ ID No. 130 | miR-492 | 2.28 | AGGACCUGCGGGACAAGAUUCUU |
| SEQ ID No. 131 | miR-362-3p | 2.27 | AACACACCUAUUCAAGGAUUCA |
| SEQ ID No. 132 | miR-197 | 2.27 | UUCACCACCUUCUCCACCCAGC |
| SEQ ID No. 133 | miR-574-5p | 2.26 | UGAGUGUGUGUGUGUGAGUGUGU |
| SEQ ID No. 134 | miR-148b | 2.26 | UCAGUGCAUCACAGAACUUUGU |
| SEQ ID No. 135 | miR-151-3p | 2.22 | CUAGACUGAAGCUCCUUGAGG |
| SEQ ID No. 136 | miR-520d-5p | 2.22 | CUACAAAGGGAAGCCCUUUC |
| SEQ ID No. 137 | miR-151-3p | 2.21 | CUAGACUGAAGCUCCUUGAGG |
| SEQ ID No. 138 | miR-675 | 2.20 | UGGUGCGGAGAGGGCCCACAGUG |
| SEQ ID No. 139 | miR-625* | 2.16 | GACUAUAGAACUUUCCCCCUCA |
| SEQ ID No. 140 | miR-516a-5p | 2.13 | UUCUCGAGGAAAGAAGCACUUUC |
| SEQ ID No. 141 | miR-129-5p | 2.11 | CUUUUUGCGGUCUGGGCUUGC |

TABLE 1-continued

| SEQ ID | miRNA | Fold induction | RNA sequence |
|---|---|---|---|
| SEQ ID No. 142 | miR-1246 | 2.10 | AAUGGAUUUUUGGAGCAGG |
| SEQ ID No. 143 | miR-193b | 2.09 | AACUGGCCCUCAAAGUCCCGCU |
| SEQ ID No. 144 | miR-1297 | 2.07 | UUCAAGUAAUUCAGGUG |
| SEQ ID No. 145 | miR-7 | 2.07 | UGGAAGACUAGUGAUUUUGUUGU |
| SEQ ID No. 146 | miR-214 | 2.06 | ACAGCAGGCACAGACAGGCAGU |
| SEQ ID No. 147 | miR-509-3-5p | 2.05 | UACUGCAGACGUGGCAAUCAUG |
| SEQ ID No. 148 | miR-744 | 2.04 | UGCGGGGCUAGGGCUAACAGCA |
| SEQ ID No. 149 | miR-518a-5p/miR-527 | 2.03 | CUGCAAAGGGAAGCCCUUUC |
| SEQ ID No. 150 | miR-498 | 2.02 | UUUCAAGCCAGGGGGCGUUUUUC |
| SEQ ID No. 151 | miR-183 | 2.02 | UAUGGCACUGGUAGAAUUCACU |
| SEQ ID No. 152 | miR-597 | 2.01 | UGUGUCACUCGAUGACCACUGU |

The invention claimed is:

1. A method for increasing blood-brain barrier function, comprising introducing to or expressing in brain endothelial cells a nucleic acid comprising a nucleic acid sequence which has at least 70% sequence identity with a sequence selected from the group consisting of SEQ ID NOs:4, 5, 7, 13, 15, 26, 32, 37, 38, 53, 60, 75, 80 and 105.

2. The method of claim 1, which is for treating stroke, brain trauma, infection, inflammation, multiple sclerosis, HIV infection, Alzheimer's disease, Parkinson's disease, epilepsy, brain tumours, glaucoma and lysosomal storage diseases, prion disease, retinal dysfunction, cerebrovascular disease, migraine, or peroxisome-associated diseases in a patient in need thereof.

3. The method according to claim 1, wherein the brain endothelial cell is a primary cell or a cell line.

4. The method according to claim 1, wherein the nucleic acid is a pre-miRNA, pri-miRNA, a siRNA or a shRNA.

5. The method according to claim 1, wherein the nucleic acid is introduced into a brain endothelial cell within a delivery vehicle.

6. The method according to claim 5, wherein the nucleic acid within the delivery vehicle is introduced in vivo.

7. The method according to claim 1, wherein the nucleic acid sequence has at least 75% sequence identity with a sequence selected from the group consisting of SEQ ID NOs: 4, 5, 7, 13, 15, 26, 32, 37, 38, 53, 60, 75, 80 and 105.

8. The method according to claim 1, wherein the nucleic acid sequence has at least 80% sequence identity with a sequence selected from the group consisting of SEQ ID NOs: 4, 5, 7, 13, 15, 26, 32, 37, 38, 53, 60, 75, 80 and 105.

9. The method according to claim 1, wherein the nucleic acid sequence has at least 85% sequence identity with a sequence selected from the group consisting of SEQ ID NOs: 4, 5, 7, 13, 15, 26, 32, 37, 38, 53, 60, 75, 80 and 105.

10. The method according to claim 1, wherein the nucleic acid sequence has at least 90% sequence identity with a sequence selected from the group consisting of SEQ ID NOs: 4, 5, 7, 13, 15, 26, 32, 37, 38, 53, 60, 75, 80 and 105.

11. The method according to claim 1, wherein the nucleic acid sequence has at least 95% sequence identity with a selected from the group consisting of SEQ ID NOs:4, 5, 7, 13, 15, 26, 32, 37, 38, 53, 60, 75, 80 and 105.

12. The method according to claim 1, wherein the nucleic acid sequence has 100% sequence identity with a sequence selected from the group consisting of SEQ ID NOs:4, 5, 7, 13, 15, 26, 32, 37, 38, 53, 60, 75, 80 and 105.

13. The method according to claim 1, wherein the sequence, to which the nucleic acid sequence comprised by the nucleic acid has at least 70% sequence identity with, is one selected from the group consisting of SEQ ID NOs:32, 37, 38, 53, and 80.

14. The method according to claim 3, wherein the brain endothelial cell is derived from a vertebrate brain endothelial cell.

15. The method according to claim 3, wherein the brain endothelial cell is derived from a human brain endothelial cell.

16. The method according to claim 3, wherein the brain endothelial cell is of cell line HCMEC/D3.

\* \* \* \* \*